United States Patent
Mezo et al.

(10) Patent No.: US 9,938,335 B2
(45) Date of Patent: Apr. 10, 2018

(54) GLUCAGON AND GLP-1 CO-AGONIST COMPOUNDS

(71) Applicant: Eli Lilly and Company, Indianapolis, IN (US)

(72) Inventors: Adam Robert Mezo, Carmel, IN (US); Yanyun Chen, Carmel, IN (US); Francisco Alcides Valenzuela, Indianapolis, IN (US); Hongchang Qu, Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 15/184,116

(22) Filed: Jun. 16, 2016

(65) Prior Publication Data

US 2016/0368960 A1 Dec. 22, 2016

Related U.S. Application Data

(60) Provisional application No. 62/182,847, filed on Jun. 22, 2015.

(51) Int. Cl.
*A61K 38/00* (2006.01)
*C07K 14/605* (2006.01)
*C07K 14/00* (2006.01)

(52) U.S. Cl.
CPC .......... *C07K 14/605* (2013.01); *C07K 14/00* (2013.01); *A61K 38/00* (2013.01); *C07K 2319/00* (2013.01)

(58) Field of Classification Search
CPC combination set(s) only.
See application file for complete search history.

(56) References Cited

FOREIGN PATENT DOCUMENTS

| CA | 2852177 A1 | 12/2009 |
|---|---|---|
| WO | 2011/075393 A2 | 6/2011 |
| WO | 2011/087672 A1 | 7/2011 |
| WO | 2011094337 A1 | 8/2011 |
| WO | 2012/177444 A2 | 12/2012 |
| WO | 2013004983 A1 | 1/2013 |
| WO | 2013074910 A1 | 5/2013 |
| WO | 2014/041195 A1 | 3/2014 |
| WO | 2014152460 A2 | 9/2014 |

OTHER PUBLICATIONS

PCT International Search Report for PCT/US2016/037818, dated Aug. 23, 2016.
Bianchi E et al., "A PEGylated analog of the gut hormone oxyntomodulin with long-lasting antihyperglycemic, insulinotropic and anorexigenic activity", Bioorganic and Medicinal Chemistry, vol. 21, pp. 7064-7073, 2013.
Day J W et al., "A new glucagon and GLP-1 co-agonist eliminates obesity in rodents", Nature Chemical Biology, vol. 5, No. 10, pp. 749-758, 2009.
Day J W et al., "Optimization of Co-Agonism at GLP-1 and Glucagon Receptors to Safely Maximize Weight Reduction in DIO-Rodents", Peptide Science, vol. 98, No. 5, pp. 443-450, 2012.
Druce M R et al., "Investigation of Structure-Activity Relationships of Oxyntomodulin (Oxm) Using Oxm Analogs", Endocrinology, vol. 150, No. 4, pp. 1712-1721, 2009.
Lorenz M et al., "Recent progress and future options in the development of GLP-1 receptor agonists for the treatment of diabesity", Bioorganic and Medicinal Chemistry Letters, vol. 23, pp. 4011-4018, 2013.
Pogai A, "Unraveling oxyntomodulin, GLP1's enigmatic brother", Journal of Endocrinology, vol. 215, pp. 335-346, 2012.
Pogai A, "Action and therapeutic potential of oxyntomodulin", Molecular Mechanism, vol. 3, pp. 241-251, 2014.
Santoprete A et al., "DPP-IV-resistant, long-acting oxyntomodulin derivatives", Journal of Peptide Science, vol. 17, pp. 270-280, 2011.

*Primary Examiner* — Gyan Chandra
(74) *Attorney, Agent, or Firm* — Jennifer K. Gregory

(57) ABSTRACT

The present invention provides glucagon and GLP-1 co-agonist compounds that are useful in the treatment of type 2 diabetes, obesity, nonalcoholic fatty liver disease (NAFLD) and/or nonalcoholic steatohepatitis (NASH).

21 Claims, No Drawings

GLUCAGON AND GLP-1 CO-AGONIST COMPOUNDS

The present invention is in the field of medicine. More particularly, the present invention is in the field of treatment of diabetes and obesity and relates to compounds that agonize both the glucagon (Gcg) receptor and the glucagon-like-peptide-1 (GLP-1) receptor. Specifically provided are oxyntomodulin/glucagon analogues with amino acid modifications introduced to modulate activity for both the Gcg receptor and the GLP-1 receptor.

Over the past several decades, the prevalence of diabetes has continued to rise. Type 2 diabetes mellitus (T2D) is the most common form of diabetes accounting for approximately 90% of all diabetes. T2D is characterized by high blood glucose levels caused by insulin resistance. The current standard of care for T2D includes diet and exercise along with available oral and injectable glucose lowering drugs. Nonetheless, many patients with T2D still remain inadequately controlled. Uncontrolled diabetes leads to several conditions that impact morbidity and mortality of patients. The leading cause of death for diabetic patients is cardiovascular complications. One of the main risk factors for type 2 diabetes is obesity. The majority of T2D patients (90%) are overweight or obese. It is documented that a decrease in body adiposity will lead to improvement in obesity-associated co-morbidities including hyperglycaemia and cardiovascular events. Therefore, therapies effective in glucose control and weight reduction are needed for better disease management.

A number of peptides derived from pre-proglucagon, and analogues thereof, have been proposed as therapeutics for the treatment of T2D and obesity, in particular, Gcg, GLP-1 and oxyntomodulin (OXM). Pre-proglucagon is a 158 amino acid precursor polypeptide that is differentially processed in the tissues to form a number of structurally related proglucagon-derived peptides, including Gcg, GLP-1, glucagon-like-peptide-2 (GLP-2), and oxyntomodulin (OXM). These molecules are involved in a wide variety of physiological functions, including glucose homeostasis, insulin secretion, gastric emptying and intestinal growth, as well as regulation of food intake.

Gcg is a 29-amino acid peptide that corresponds to amino acids 53 to 81 of preproglucagon. OXM is a 37 amino acid peptide and is composed of the complete 29 amino acid sequence of Gcg with an octapeptide carboxy terminal extension (amino acids 82 to 89 of pre-proglucagon and termed "intervening peptide 1" or IP-1). The major biologically active fragment of GLP-1 (GLP-1$_{7-36}$) is produced as a 30-amino acid, C-terminal amidated peptide that corresponds to amino acids 98 to 127 of pre-proglucagon.

Gcg helps maintain the level of glucose in the blood by binding to Gcg receptors on hepatocytes, causing the liver to release glucose—stored in the form of glycogen—through glycogenolysis. As these stores become depleted, Gcg stimulates the liver to synthesize additional glucose by gluconeogenesis. This glucose is released into the bloodstream, preventing the development of hypoglycaemia.

GLP-1 has different biological activities compared to Gcg. Its actions include stimulation of insulin synthesis and secretion, inhibition of Gcg secretion and inhibition of food intake. GLP-1 has been shown to reduce hyperglycaemia in diabetics. Several GLP-1 agonists have been approved for use in the treatment of T2D in humans, including exenatide, liraglutide, lixisenatide, albiglutide and dulaglutide. Such GLP-1 agonists are effective in glycaemic control with favourable effects on weight without the risk of hypoglycaemia. However, the weight loss is modest due to dose-dependent gastrointestinal side-effects.

OXM is released along with GLP-1 from the L-cells of the small intestine in proportion to nutrient ingestion. OXM activates both the Gcg and GLP-1 receptors, with a slightly higher potency for the Gcg receptor over the GLP-1 receptor. It is less potent than native Gcg and GLP-1 on their respective receptors. Human Gcg is also capable of activating both receptors, albeit with a strong preference for the Gcg receptor over the GLP-1 receptor. GLP-1 is not capable of activating Gcg receptors. OXM is involved in regulation of food intake and body weight. It has been shown to suppress appetite and inhibit food intake in humans. In a 4-week study with overweight and obese subjects, three times daily preprandial subcutaneous administration of OXM produced a weight loss of 2.3 kg compared with 0.5 kg in the placebo group. In this trial, nausea, the most common side-effect associated with GLP-1 based therapy (such as exenatide and liraglutide), was less frequent. In another shorter study, OXM was shown to decrease caloric intake and increase activity-related energy expenditure in overweight and obese subjects.

These data suggest that OXM has the potential of being a well-tolerated anti-diabetes/obesity agent. OXM, however, presents several challenges for development into a commercially-viable therapeutic agent. Endogenous OXM is quickly degraded in vivo by dipeptidyl peptidase IV and other peptidases as well as being subject to rapid renal clearance due to its small size. It is therefore desirable to identify peptides that activate the Gcg and GLP-1 receptors with improved metabolic stability and reduced rate of clearance.

OXM peptides with amino acid substitutions to improve stability and with additional modifications to slow clearance, such as PEGylation or lipidation are disclosed in the art. Other peptides have been stated to bind to and activate both the Gcg receptor and the GLP-1 receptor and to suppress body weight gain (see for example, WO 2011/075393 A2 and WO 2012/177444 A2).

Despite the availability of various peptides that agonize both the Gcg and GLP-1 receptors, there remains a need for more potent, stable, long-acting, and/or well-tolerated compounds having a ratio of Gcg receptor (Gcg-R)/GLP-1 receptor (GLP-1-R) activity that has been optimized such that the potency and insulinotropic activity of the compounds provides effective treatments for diabetes, preferably T2D, and related disorders. In particular, there remains a need for compounds with a balanced ratio of Gcg-R/GLP-1-R coagonist activity that reduce body weight. Also, there remains a need to provide compounds with a balanced ratio of Gcg-R/GLP-1-R co-agonist activity that supports potential daily, bi-weekly, once-weekly or monthly dosing in humans. Accordingly, the present invention seeks to provide effective treatments for diabetes, obesity, nonalcoholic fatty liver disease (NAFLD) and/or nonalcoholic steatohepatitis (NASH).

In one aspect, the present invention provides a compound of the following formula:

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Xaa28-Gly-Gly-Pro-Ser-Ser-Gly wherein
Xaa2 is Aib;
Xaa28 is Glu or Ser;

Lys at position 20 is chemically modified by conjugation of the epsilon-amino group of the Lys side chain with a C14-C24 fatty acid via (i) a direct bond or (ii) a linker between the Lys at position 20 and the C14-C24 fatty acid; and the C-terminal amino acid is optionally amidated (SEQ ID NO: 2), or a pharmaceutically acceptable salt thereof.

In another aspect, the present invention provides a compound of the following formula:

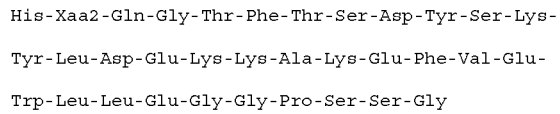
```
His-Xaa2-Gln-Gly-Thr-Phe-Thr-Ser-Asp-Tyr-Ser-Lys-
Tyr-Leu-Asp-Glu-Lys-Lys-Ala-Lys-Glu-Phe-Val-Glu-
Trp-Leu-Leu-Glu-Gly-Gly-Pro-Ser-Ser-Gly
``` wherein
Xaa2 is Aib;
Lys at position 20 is chemically modified by conjugation of the epsilon-amino group of the Lys side chain with a C14-C24 fatty acid via (i) a direct bond or (ii) a linker between the Lys at position 20 and the C14-C24 fatty acid; and the C-terminal amino acid is optionally amidated (SEQ ID NO: 3), or a pharmaceutically acceptable salt thereof.

In yet another aspect, the present invention provides a compound of the following formula:

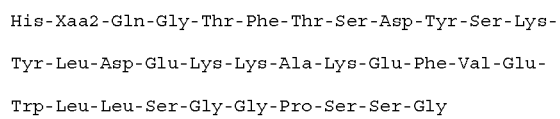
```
His-Xaa2-Gln-Gly-Thr-Phe-Thr-Ser-Asp-Tyr-Ser-Lys-
Tyr-Leu-Asp-Glu-Lys-Lys-Ala-Lys-Glu-Phe-Val-Glu-
Trp-Leu-Leu-Ser-Gly-Gly-Pro-Ser-Ser-Gly
``` wherein
Xaa2 is Aib;
Lys at position 20 is chemically modified by conjugation of the epsilon-amino group of the Lys side chain with a C14-C24 fatty acid via (i) a direct bond or (ii) a linker between the Lys at position 20 and the C14-C24 fatty acid; and the C-terminal amino acid is optionally amidated (SEQ ID NO: 4), or a pharmaceutically acceptable salt thereof.

In a preferred aspect of the compounds of the present invention, or pharmaceutically acceptable salts thereof, the Lys at position 20 is chemically modified by conjugation with a C14-C24 fatty acid via a linker between the Lys at position 20 and the C14-C24 fatty acid.

Further preferably, the linker is selected from the group consisting of:

(a) an amino polyethylene glycol carboxylate of Formula I:

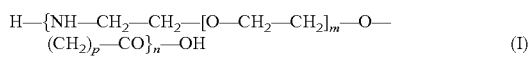

$$H-\{NH-CH_2-CH_2-[O-CH_2-CH_2]_m-O-(CH_2)_p-CO\}_n-OH \qquad (I)$$

wherein m is any integer from 1 to 12, n is any integer from 1 to 12, and p is 1 or 2;

(b) an amino acid selected from the group consisting of arginine (Arg), asparagine (Asn), aspartic acid (Asp), glutamine (Gln), glutamic acid (Glu), histidine (His), lysine (Lys), serine (Ser), threonine (Thr), citrulline (Cit), ornithine (Orn), sarcosine (Sar), glycine (Gly), γ-aminobutyric acid (γ-Abu) and γ-glutamic acid (γ-Glu);

(c) a dipeptide selected from the group consisting of Ala-Ala, β-Ala-β-Ala, Glu-Glu, Gly-Gly, Leu-Leu, Ser-Ser, Thr-Thr, γ-Glu-γ-Glu, Glu-γ-Glu, γ-Glu-Glu, γ-Glu-Glu, γ-Abu-γ-Abu, 6-aminohexanoic acid-6-aminohexanoic acid, 5-aminovaleric acid-5-aminovaleric acid, 7-aminoheptanoic acid-7-aminoheptanoic acid and 8-aminooctanoic acid-8-aminooctanoic acid;

(d) a tripeptide selected from the group consisting of Ala-Ala-Ala, β-Ala-β-Ala-β-Ala, Glu-Glu-Glu, γ-Glu-γ-Glu-γ-Glu, Glu-γ-Glu-γ-Glu, γ-Glu-γ-Glu-Glu, γ-Glu-Glu-γ-Glu, Gly-Gly-Gly, Gly-Gly-Ser, Ser-Gly-Gly, Gly-Ser-Gly, Gly-Gly-Glu, Glu-Gly-Gly, Gly-Glu-Gly, Gly-Gly-γ-Glu, γ-Glu-Gly-Gly, Gly-γ-Glu-Gly, Leu-Leu-Leu and γ-Abu-γ-Abu-γ-Abu;

(e) a polypeptide selected from the group consisting of (Gly-Gly-Ser)$_q$, (Gly-Gly-Gly-Ser)$_r$, and (Gly-Gly-Gly-Gly-Ser)$_r$, (6-aminohexanoic acid)$_s$, (5-aminovaleric acid)$_s$, (7-aminoheptanoic acid)$_s$, and (8-aminooctanoic acid)$_s$, where q is any integer from 2 to 5, r is any integer from 1 to 3, and s is any integer from 4 to 15; and (f) a conjugate linker wherein an amino polyethylene glycol carboxylate of Formula I as defined in (a) is conjugated with:

(i) an amino acid selected from the group consisting of Arg, Asn, Asp, Gln, Glu, His, Lys, Ser, Thr, Cit, Orn, Sar, Gly, γ-Abu and γ-Glu;

(ii) a dipeptide selected from the group consisting of Ala-Ala, β-Ala-β-Ala, Glu-Glu, Gly-Gly, Leu-Leu, Ser-Ser, Thr-Thr, γ-Glu-γ-Glu, Glu-γ-Glu, γ-Glu-Glu, γ-Abu-γ-Abu, 6-aminohexanoic acid-6-aminohexanoic acid, 5-aminovaleric acid-5-aminovaleric acid, 7-aminoheptanoic acid-7-aminoheptanoic acid and 8-aminooctanoic acid-8-aminooctanoic acid;

(iii) a tripeptide selected from the group consisting of Ala-Ala-Ala, β-Ala-β-Ala-β-Ala, Glu-Glu-Glu, γ-Glu-γ-Glu-γ-Glu, Glu-γ-Glu-γ-Glu, γ-Glu-γ-Glu-Glu, γ-Glu-Glu-γ-Glu, Gly-Gly-Gly, Gly-Gly-Ser, Ser-Gly-Gly, Gly-Ser-Gly, Gly-Gly-Glu, Glu-Gly-Gly, Gly-Glu-Gly, Gly-Gly-γ-Glu, γ-Glu-Gly-Gly, Gly-γ-Glu-Gly, Leu-Leu-Leu and γ-Abu-γ-Abu-γ-Abu; or (iv) a polypeptide selected from the group is selected from the group consisting of (Gly-Gly-Ser)$_q$, (Gly-Gly-Gly-Ser)$_r$, and (Gly-Gly-Gly-Gly-Ser)$_r$, (6-aminohexanoic acid)$_s$, (5-aminovaleric acid)$_s$, (7-aminoheptanoic acid)$_s$, and (8-aminooctanoic acid)$_s$, where q is any integer from 2 to 5, r is any integer from 1 to 3, and s is any integer from 4 to 15.

In a preferred aspect of the compounds of the present invention, or pharmaceutically acceptable salts thereof, the linker is an amino polyethylene glycol carboxylate of Formula I:

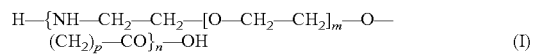

$$H-\{NH-CH_2-CH_2-[O-CH_2-CH_2]_m-O-(CH_2)_p-CO\}_n-OH \qquad (I)$$

wherein m is any integer from 1 to 12, n is any integer from 1 to 12, and p is 1 or 2.

Preferably, n is 1, 2, 3, 4, 5 or 6 and m is 1 and p is 1 for the amino polyethylene glycol carboxylate of Formula I.

Further preferably, n is 2, m is 1 and p is 1 for the amino polyethylene glycol carboxylate of Formula I.

In a further preferred aspect of the compounds of the present invention, or pharmaceutically acceptable salts thereof, the linker is an amino acid selected from the group consisting of Arg, Asn, Asp, Gln, Glu, His, Lys, Ser, Thr, Cit, Orn, Sar, Gly, γ-Abu and γ-Glu.

Preferably, the amino acid is γ-Glu.

In a still further preferred aspect of the compounds of the present invention, or pharmaceutically acceptable salts thereof, the linker is a dipeptide selected from the group consisting of Ala-Ala, β-Ala-β-Ala, Glu-Glu, Gly-Gly, Leu-Leu, Ser-Ser, Thr-Thr, γ-Glu-γ-Glu, Glu-γ-Glu, γ-Glu-Glu, γ-Abu-γ-Abu, 6-aminohexanoic acid-6-aminohexanoic acid, 5-aminovaleric acid-5-aminovaleric acid, 7-aminoheptanoic acid-7-aminoheptanoic acid and 8-aminooctanoic acid-8-aminooctanoic acid.

Preferably, the dipeptide is γ-Glu-γ-Glu.

In a still further preferred aspect of the compounds of the present invention, or pharmaceutically acceptable salts thereof, the linker is a tripeptide is selected from the group consisting of Ala-Ala-Ala, β-Ala-β-Ala-β-Ala, Glu-Glu-Glu, γ-Glu-γ-Glu-γ-Glu, Glu-γ-Glu-γ-Glu, γ-Glu-γ-Glu-Glu, γ-Glu-Glu-γ-Glu, Gly-Gly-Gly, Gly-Gly-Ser, Ser-Gly-Gly, Gly-Ser-Gly, Gly-Gly-Glu, Glu-Gly-Gly, Gly-Glu-Gly, Gly-Gly-γ-Glu, γ-Glu-Gly-Gly, Gly-γ-Glu-Gly, Leu-Leu-Leu and γ-Abu-γ-Abu-γ-Abu.

In a still further preferred aspect of the compounds of the present invention, or pharmaceutically acceptable salts thereof, the linker is a polypeptide is selected from the group consisting of (Gly-Gly-Ser)$_q$, (Gly-Gly-Gly-Ser)$_r$, and (Gly-Gly-Gly-Gly-Ser)$_r$, (6-aminohexanoic acid)$_s$, (5-aminovaleric acid)$_s$, (7-aminoheptanoic acid)$_s$, and (8-aminooctanoic acid)$_s$, where q is any integer from 2 to 5, r is any integer from 1 to 3, and s is any integer from 4 to 15.

In a still further preferred aspect of the compounds of the present invention, or pharmaceutically acceptable salts thereof, the linker is a conjugate linker, wherein an amino polyethylene glycol carboxylate of Formula I:

$$H-\{NH-CH_2-CH_2-[O-CH_2-CH_2]_m-O-(CH_2)_p-CO\}_n-OH \quad (I)$$

wherein m is any integer from 1 to 12, n is any integer from 1 to 12, and p is 1 or 2, is conjugated with:
(i) an amino acid selected from the group consisting of Arg, Asn, Asp, Gln, Glu, His, Lys Ser, Thr, Cit, Orn, Sar, Gly, γ-Abu and γ-Glu;
(ii) a dipeptide selected from the group consisting of Ala-Ala, β-Ala-β-Ala, Glu-Glu, Gly-Gly, Leu-Leu, Ser-Ser, Thr-Thr, γ-Glu-γ-Glu, Glu-γ-Glu, γ-Glu-Glu, γ-Abu-γ-Abu, 6-aminohexanoic acid-6-aminohexanoic acid, 5-aminovaleric acid-5-aminovaleric acid, 7-aminoheptanoic acid-7-aminoheptanoic acid and 8-aminooctanoic acid-8-aminooctanoic acid;
(iii) a tripeptide selected from the group consisting of Ala-Ala-Ala, β-Ala-β-Ala-β-Ala, Glu-Glu-Glu, γ-Glu-γ-Glu-γ-Glu, Glu-γ-Glu-γ-Glu, γ-Glu-γ-Glu-Glu, γ-Glu-Glu-γ-Glu, Gly-Gly-Gly, Gly-Gly-Ser, Ser-Gly-Gly, Gly-Ser-Gly, Gly-Gly-Glu, Glu-Gly-Gly, Gly-Glu-Gly, Gly-Gly-γ-Glu, γ-Glu-Gly-Gly, Gly-γ-Glu-Gly, Leu-Leu-Leu and γ-Abu-γ-Abu-γ-Abu; or
(iv) a polypeptide selected from the group consisting of (Gly-Gly-Ser)$_q$, (Gly-Gly-Gly-Ser)$_r$, and (Gly-Gly-Gly-Gly-Ser)$_r$, (6-aminohexanoic acid)$_s$, (5-aminovaleric acid)$_s$, (7-aminoheptanoic acid)$_s$, and (8-aminooctanoic acid)$_s$, where q is any integer from 2 to 5, r is any integer from 1 to 3, and s is any integer from 4 to 15. Preferably, n is 1, 2, 3, 4, 5 or 6 and m is 1 and p is 1 for amino polyethylene glycol carboxylate of Formula I.

Further preferably, n is 2, m is 1 and p is 1 for the amino polyethylene glycol carboxylate of Formula I.

Still further preferably, the amino acid is γ-Glu.

Still further preferably, the dipeptide is γ-Glu-γ-Glu.

In a preferred aspect of the compounds of the present invention, the linker is ([2-(2-aminoethoxy)-ethoxy]-acetyl)$_2$-(γ-Glu)$_t$, wherein t is 1 or 2.

Preferably, t is 1.

Further preferably, t is 2.

In a still further preferred aspect of the compounds of the present invention, or pharmaceutically acceptable salts thereof, the C14-C24 fatty acid is a saturated monoacid or a saturated diacid.

Preferably, the fatty acid is a saturated monoacid or saturated diacid selected from the group consisting of myristic acid (tetradecanoic acid)(C14 monoacid), tetradecanedioic acid (C14 diacid), palmitic acid (hexadecanoic acid)(C16 monoacid), hexadecanedioic acid (C16 diacid), margaric acid (heptadecanoic acid)(C17 monoacid), heptadecanedioic acid (C17 diacid), stearic acid (octadecanoic acid)(C18 monoacid), octadecanedioic acid (C18 diacid), nonadecylic acid (nonadecanoic acid)(C19 monoacid), nonadecanedioic acid (C19 diacid), arachadic acid (eicosanoic acid)(C20 monoacid), eicosanedioic acid (C20 diacid), heneicosylic acid (heneicosanoic acid)(C21 monoacid), heneicosanedioic acid (C21 diacid), behenic acid (docosanoic acid)(C22), docosanedioic acid (C22 diacid), lignoceric acid (tetracosanoic acid)(C24 monoacid) and tetracosanedioic acid (C24 diacid).

Still further preferably, the C14-C24 fatty acid is myristic acid

Still further preferably, the C14-C24 fatty acid is tetradecanedioic acid.

Still further preferably, the C14-C24 fatty acid is palmitic acid.

Still further preferably, the C14-C24 fatty acid is hexadecanedioic acid.

Still further preferably, the C14-C24 fatty acid is stearic acid.

Still further preferably, the C14-C24 fatty acid is octadecanedioic acid.

Still further preferably, the C14-C24 fatty acid is nonadecanedioic acid.

Still further preferably, the C14-C24 fatty acid is arachadic acid.

Still further preferably, the C14-C24 fatty acid is eicosanedioic acid.

Still further preferably, the C14-C24 fatty acid is docosanedioic acid.

In a still further preferred aspect of the compounds of the present invention, or pharmaceutically acceptable salts thereof, the C-terminal amino acid is amidated.

In a further aspect, the present invention provides a compound of the following formula:

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Glu-Gly-Gly-Pro-Ser-Ser-Gly wherein Xaa 2 is Aib;
Lys at position 20 is chemically modified by conjugation of the epsilon-amino group of the Lys side chain with ([2-(2-aminoethoxy)-ethoxy]-acetyl)$_2$-(γ-Glu)-CO—(CH$_2$)$_{16}$ CO$_2$H; and
the C-terminal amino acid is amidated (SEQ ID NO: 5), or a pharmaceutically acceptable salt thereof.

In a further aspect, the present invention provides a compound of the following formula:

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Glu-Gly-Gly-Pro-Ser-Ser-Gly wherein Xaa 2 is Aib;
Lys at position 20 is chemically modified by conjugation of the epsilon-amino group of the Lys side chain with ([2-(2-aminoethoxy)-ethoxy]-acetyl)$_2$-(γ-Glu)-CO—(CH$_2$)$_{18}$ CO$_2$H; and
the C-terminal amino acid is amidated (SEQ ID NO: 6); or a pharmaceutically acceptable salt thereof.

In a further aspect, the present invention provides a compound of the following formula:

His-Xaa2-Gln-Gly-Thr-Phe-Thr-Ser-Asp-Tyr-Ser-Lys-
Tyr-Leu-Asp-Glu-Lys-Lys-Ala-Lys-Glu-Phe-Val-Glu-
Trp-Leu-Leu-Ser-Gly-Gly-Pro-Ser-Ser-Gly wherein Xaa 2 is Aib;
Lys at position 20 is chemically modified by conjugation of the epsilon-amino group of the Lys side chain with ([2-(2-aminoethoxy)-ethoxy]-acetyl)$_2$-($\gamma$-Glu)$_2$-CO—(CH$_2$)$_{16}$ CO$_2$H; and
the C-terminal amino acid is amidated (SEQ ID NO: 7);
or a pharmaceutically acceptable salt thereof.

In a further aspect, the present invention provides a compound of the following formula:

His-Xaa2-Gln-Gly-Thr-Phe-Thr-Ser-Asp-Tyr-Ser-Lys-
Tyr-Leu-Asp-Glu-Lys-Lys-Ala-Lys-Glu-Phe-Val-Glu-
Trp-Leu-Leu-Ser-Gly-Gly-Pro-Ser-Ser-Gly wherein Xaa 2 is Aib;
Lys at position 20 is chemically modified by conjugation of the epsilon-amino group of the Lys side chain with ([2-(2-aminoethoxy)-ethoxy]-acetyl)$_2$-($\gamma$-Glu)$_2$-CO—(CH$_2$)$_{18}$ CO$_2$H; and
the C-terminal amino acid is amidated (SEQ ID NO: 8);
or a pharmaceutically acceptable salt thereof.

In a further aspect, the present invention provides a pharmaceutical composition comprising a compound of the present invention, or a pharmaceutically acceptable salt thereof, and a pharmaceutically acceptable carrier, diluent, or excipient.

In a further aspect, the present invention provides a pharmaceutical composition comprising a compound of the present invention, or a pharmaceutically acceptable salt thereof, together with a pharmaceutically acceptable carrier, diluent, or excipient and other therapeutic ingredients.

In a still further aspect, the present invention provides a method of treating type 2 diabetes in a subject in need thereof, comprising administering to the subject an effective amount of a compound of the present invention, or a pharmaceutically acceptable salt thereof.

In a still further aspect, the present invention provides a method of treating obesity in a subject in need thereof, comprising administering to the subject an effective amount of a compound of the present invention, or a pharmaceutically acceptable salt thereof.

In a still further aspect, the present invention provides a method of treating nonalcoholic fatty liver disease (NAFLD) in a subject in need thereof, comprising administering to the subject an effective amount of a compound of the present invention, or a pharmaceutically acceptable salt thereof.

In a still further aspect, the present invention provides a method of treating nonalcoholic steatohepatitis (NASH) in a subject in need thereof, comprising administering to the subject an effective amount of a compound of the present invention, or a pharmaceutically acceptable salt thereof.

In a still further aspect, the present invention provides a method of inducing non-therapeutic weight-loss in a subject comprising administration of an effective amount of a compound of the present invention, or a pharmaceutically acceptable salt thereof.

In a still further aspect, the present invention provides a compound of the present invention for use in therapy.

In a still further aspect, the present invention provides a compound of the present invention for use in the treatment of type 2 diabetes.

In a still further aspect, the present invention provides a compound of the present invention for use in the treatment of obesity.

In a still further aspect, the present invention provides a compound of the present invention for use in the treatment of nonalcoholic fatty liver disease (NAFLD).

In a still further aspect, the present invention provides a compound of the present invention for use in the treatment of nonalcoholic steatohepatitis (NASH).

In a still further aspect, the present invention provides the use of a compound of the present invention for the manufacture of a medicament for the treatment of type 2 diabetes.

In a still further aspect, the present invention provides the use of a compound of the present invention for the manufacture of a medicament for the treatment of obesity.

In a still further aspect, the present invention provides the use of a compound of the present invention for the manufacture of a medicament for the treatment of nonalcoholic fatty liver disease (NAFLD).

In a still further aspect, the present invention provides the use of a compound of the present invention for the manufacture of a medicament for the treatment of nonalcoholic steatohepatitis (NASH).

In a still further aspect, the present invention provides a compound of the following formula:

His-Xaa2-Gln-Gly-Thr-Phe-Thr-Ser-Asp-Tyr-Ser-Lys-
Tyr-Leu-Asp-Glu-Lys-Lys-Ala-Lys-Glu-Phe-Val-Glu-
Trp-Leu-Leu-Xaa28-Gly-Gly-Pro-Ser-Ser-Gly wherein Xaa 2 is Aib;
Xaa28 is Glu or Ser (SEQ ID NO: 9); and
the C-terminal amino acid is optionally amidated,
or a pharmaceutically acceptable salt thereof.

Preferably, the present invention provides a compound of the following formula:

His-Xaa2-Gln-Gly-Thr-Phe-Thr-Ser-Asp-Tyr-Ser-Lys-
Tyr-Leu-Asp-Glu-Lys-Lys-Ala-Lys-Glu-Phe-Val-Glu-
Trp-Leu-Leu-Glu-Gly-Gly-Pro-Ser-Ser-Gly wherein Xaa 2 is Aib; and
the C-terminal amino acid is optionally amidated (SEQ ID NO: 10);
or a pharmaceutically acceptable salt thereof.

Further preferably, the present invention provides a compound of the following formula:

His-Xaa2-Gln-Gly-Thr-Phe-Thr-Ser-Asp-Tyr-Ser-Lys-
Tyr-Leu-Asp-Glu-Lys-Lys-Ala-Lys-Glu-Phe-Val-Glu-
Trp-Leu-Leu-Ser-Gly-Gly-Pro-Ser-Ser-Gly wherein Xaa 2 is Aib; and
the C-terminal amino acid is optionally amidated (SEQ ID NO: 11),
or a pharmaceutically acceptable salt thereof.

In a still further aspect, the present invention provides a process for the manufacture of a compound of the following formula:

His-Xaa2-Gln-Gly-Thr-Phe-Thr-Ser-Asp-Tyr-Ser-Lys-
Tyr-Leu-Asp-Glu-Lys-Lys-Ala-Lys-Glu-Phe-Val-Glu-
Trp-Leu-Leu-Xaa28-Gly-Gly-Pro-Ser-Ser-Gly wherein Xaa 2 is Aib; and
Xaa28 is Glu or Ser;
Lys at position 20 is chemically modified by conjugation of the epsilon-amino group of the Lys side chain with a C14-C24 fatty acid via (i) a direct bond or (ii) a linker between the Lys at position 20 and the C14-C24 fatty acid; and
the C-terminal amino acid is optionally amidated (SEQ ID NO: 2), or a pharmaceutically acceptable salt thereof, said process comprising the step of:
(i) modifying a compound of the following formula:

His-Xaa2-Gln-Gly-Thr-Phe-Thr-Ser-Asp-Tyr-Ser-Lys-
Tyr-Leu-Asp-Glu-Lys-Lys-Ala-Lys-Glu-Phe-Val-Glu-
Trp-Leu-Leu-Xaa28-Gly-Gly-Pro-Ser-Ser-Gly wherein Xaa2 is Aib;
Xaa28 is Glu or Ser; and
the C-terminal amino acid is optionally amidated (SEQ ID NO: 9), by conjugating the epsilon-amino group of the Lys side chain at position 20 of the intermediate compound with a C14-C24 fatty acid, optionally via a linker.

Preferably, the Lys at position 20 of the intermediate compound is modified by conjugation with a C14-C24 fatty acid via a linker between the Lys at position 20 and the C14-C24 fatty acid.

In a still further aspect, the present invention provides a compound produced by the above-described process.

The compounds of the present invention are capable of binding to and activating both the GLP-1 receptor and the Gcg receptor. The compounds of the present invention are capable of causing a reduction in food intake in overweight and obese subjects. The compounds of the invention have potential to provide superior weight loss effect versus wild type human OXM.

The compounds of the invention may improve glucose tolerance and lipid profile in subjects with T2D and/or related metabolic disturbances and may do so more effectively than wild type human OXM.

A particular advantage of the compounds of the present invention is that the frequency of side-effects, such as nausea, which is commonly associated with GLP-1 therapy, such as exenatide and liraglutide, may be reduced or eliminated. The compounds of the present invention thus may have reduced side-effects compared to GLP-1 therapy.

The compounds of the present invention comprise a polypeptide conjugated to a fatty acid. Fatty acids, through their albumin binding motifs, can improve the pharmacokinetics of a peptide by extending the plasma half-life and reducing the rate of clearance. While the compounds of the present invention would be expected to exhibit an improved pharmacokinetic profile relative to wild type human OXM, the magnitude of the improvement is not predictable. The inventors have discovered that the length, composition and position of the fatty acid, and optionally, the linker, in the compounds of the present invention results in compounds with a desirable pharmacokinetic profile that supports daily, bi-weekly, once-weekly or monthly dosing.

In addition to the improved pharmacokinetic profile, the present inventors have also discovered that the length, composition and position of the fatty acid, and optionally, the linker, are critical to the optimization of the ratio of Gcg-R/GLP-1-R co-agonist activity.

Wild type human OXM has full efficacy and potency at the human GLP-1-R and human Gcg-R. The amino acid sequence of wild type human OXM is provided below:
His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala (SEQ ID NO: 1)

Certain compounds of the present invention have a balanced ratio of Gcg-R/GLP-1-R co-agonist activity. Balanced Gcg and GLP-1 activity as used herein refers to a compound that has affinity for Gcg and GLP-1 receptors in an in vitro binding assay that is close to 1:1, such as 1:1 GLP-1/Gcg, 2:1 GLP-1/Gcg, 3:2 GLP-1/Gcg, 1:2 GLP-1/Gcg, or 2:3 GLP-1/Gcg. The research performed by the inventors revealed that the length, composition and position of the fatty acid are critical to achieving the balanced ratio of Gcg-R/GLP-1-R co-agonist activity that is a characteristic of the compounds of the present invention, as well as impacting the plasma half-life, physical stability, solubility and in vivo stability of the compounds of the present invention.

While conjugation of a peptide with a fatty acid has advantages in respect of an improved pharmacokinetic profile and/or balanced ratio of Gcg-R/GLP-1-R co-agonist activity, it would also be expected that the compound may lose activity as there is potential for interference with the binding interface of either the Gcg receptor or the GLP-1 receptor. It has been found, however, that conjugation of the Lysine residue at position 20 with a fatty acid retains activity in vitro and in vivo at both receptors to a greater extent than is the case when amino acids at other positions are conjugated with a fatty acid.

Furthermore, several amino acid substitutions relative to wild type human OXM in the claimed compounds are capable of enhancing potency at the Gcg-R and/or GLP-1-R, thereby offsetting the potency loss due to conjugation with the fatty acid while maintaining an appropriate ratio of Gcg-R/GLP-1-R co-agonist activity. It is important to note that a substitution of one amino acid residue in a particular protein may affect the characteristics of the proteins as a whole, and that overall effect may be beneficial or detrimental to the pharmacological potency and/or pharmaceutical stability. Certain amino acid substitutions may increase potency but have a detrimental effect on the stability of the molecule and vice versa. The amino acid substitutions in the compounds of the present invention relative to wild type human OXM (SEQ ID NO: 1) include S2Aib, S16E, R17K, R18K, Q20K, D21E, Q24E, M27L, N28E or N28S and T29G. In addition, the C-terminal sequence of OXM, KRNRNNIA, has been replaced with a GPSSG C-terminal sequence.

The S2Aib substitution protects the peptide from degradation by peptidases, in particular, dipeptidyl peptidase IV. The S16E, R17K, R18K and Q20K substitutions are capable of improving the potency of the compounds of the invention in in vitro assays and in vivo animal models. The D21E and Q24E substitutions are capable of improving the stability of the compounds of the invention and modulating the in vitro activity. The M27L substitution is capable of protecting the peptide from oxidation of the methionine residue. The N28E substitution is capable of improving the solubility of the compounds comprising that substitution. The N28S substitution is also capable of improving the solubility of the compounds comprising that substitution but not to the same extent as the N28E substitution. However, the solubility of compounds comprising a N28S substitution may be improved by selection of an appropriate linker. The substitution of the asparagine residue at position 28 avoids the possibility of deamidation occurring at this position.

Removal of the residues of the C-terminal sequence of OXM, KRNRNNIA, may improve solubility, which is attributable to the removal of the arginine residues. The inventors assessed compounds having (i) no C-terminal sequence, (ii) compounds with a GPSSG C-terminal sequence and (iii) compounds with a GPSSGAPPPS C-terminal sequence. It was surprisingly found that certain compounds with a GPSSG C-terminal sequence exhibited improved in vivo potency in animal models relative to wild type human OXM, compounds with no C-terminal sequence and compounds with a GPSSGAPPPS C-terminal sequence. The GPSSG C-terminal sequence also improved the stability and solubility of the compounds according to the invention relative to wild type human OXM and compounds with no C-terminal sequence.

The compounds of the present invention thus contain amino acid substitutions that, separately or together, not only are capable of improving potency, but are also capable of providing improved physical stability and solubility characteristics and increased in vivo stability.

In some aspects of the compounds of the present invention, the C14-C24 fatty acid is conjugated to the epsilon-amino group of the lysine side-chain via a linker, wherein the linker is selected from the group consisting of:
(a) an amino polyethylene glycol carboxylate of Formula I:

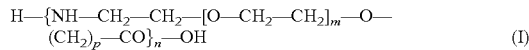

wherein m is any integer from 1 to 12, n is any integer from 1 to 12, and p is 1 or 2;
(b) an amino acid selected from the group consisting of Arg, Asn, Asp, Gln, Glu, His, Lys, Pro, Ser, Thr, Cit, Orn, Sar, Gly, γ-Abu and γ-Glu;
(c) a dipeptide selected from the group consisting of Ala-Ala, β-Ala-β-Ala, Glu-Glu, Gly-Gly, Leu-Leu, Pro-Pro, Ser-Ser, Thr-Thr, γ-Glu-γ-Glu, Glu-γ-Glu, γ-Glu-Glu, γ-Abu-γ-Abu, 6-aminohexanoic acid-6-aminohexanoic acid, 5-aminovaleric acid-5-aminovaleric acid, 7-aminoheptanoic acid-7-aminoheptanoic acid and 8-aminooctanoic acid-8-aminooctanoic acid;
(d) a tripeptide selected from the group consisting of Ala-Ala-Ala, β-Ala-β-Ala-β-Ala, Glu-Glu-Glu, γ-Glu-γ-Glu-γ-Glu, Glu-γ-Glu-γ-Glu, γ-Glu-γ-Glu-Glu, γ-Glu-Glu-γ-Glu, Gly-Gly-Gly, Gly-Gly-Ser, Ser-Gly-Gly, Gly-Ser-Gly, Gly-Gly-Glu, Glu-Gly-Gly, Gly-Glu-Gly, Gly-Gly-γ-Glu, γ-Glu-Gly-Gly, Gly-γ-Glu-Gly, Leu-Leu-Leu, Pro-Pro-Pro and γ-Abu-γ-Abu-γ-Abu;
(e) a polypeptide selected from the group is selected from the group consisting of (Gly-Gly-Ser)$_q$, (Gly-Gly-Gly-Ser)$_r$, and (Gly-Gly-Gly-Gly-Ser)$_r$, (6-aminohexanoic acid)$_s$, (5-aminovaleric acid)$_s$, (7-aminoheptanoic acid)$_s$, and (8-aminooctanoic acid)$_s$, where q is any integer from 2 to 5, r is any integer from 1 to 3, and s is any integer from 4 to 15; and
(f) a conjugate linker wherein an amino polyethylene glycol carboxylate of Formula I as defined in (a) is conjugated with:

(i) an amino acid selected from the group consisting of Arg, Asn, Asp, Gln, Glu, His, Lys, Pro, Ser, Thr, Cit, Orn, Sar, Gly, γ-Abu and γ-Glu;
(ii) a dipeptide selected from the group consisting of Ala-Ala, β-Ala-β-Ala, Glu-Glu, Gly-Gly, Leu-Leu, Pro-Pro, Ser-Ser, Thr-Thr, γ-Glu-γ-Glu, Glu-γ-Glu, γ-Glu-Glu, γ-Abu-γ-Abu, 6-aminohexanoic acid-6-aminohexanoic acid, 5-aminovaleric acid-5-aminovaleric acid, 7-aminoheptanoic acid-7-aminoheptanoic acid and 8-aminooctanoic acid-8-aminooctanoic acid;
(iii) a tripeptide selected from the group consisting of Ala-Ala-Ala, β-Ala-β-Ala-β-Ala, Glu-Glu-Glu, γ-Glu-γ-Glu-γ-Glu, Glu-γ-Glu-γ-Glu, γ-Glu-γ-Glu-Glu, γ-Glu-Glu-γ-Glu, Gly-Gly-Gly, Gly-Gly-Ser, Ser-Gly-Gly, Gly-Ser-Gly, Gly-Gly-Glu, Glu-Gly-Gly, Gly-Glu-Gly, Gly-Gly-γ-Glu, γ-Glu-Gly-Gly, Gly-γ-Glu-Gly, Leu-Leu-Leu, Pro-Pro-Pro and γ-Abu-γ-Abu-γ-Abu; or
(iv) a polypeptide selected from the group is selected from the group consisting of (Gly-Gly-Ser)$_q$, (Gly-Gly-Gly-Ser)$_r$, and (Gly-Gly-Gly-Gly-Ser)$_r$, (6-aminohexanoic acid)$_s$, (5-aminovaleric acid)$_s$, (7-aminoheptanoic acid)$_s$, and (8-aminooctanoic acid)$_s$, where q is any integer from 2 to 5, r is any integer from 1 to 3, and s is any integer from 4 to 15.

In preferred aspects of the compounds of the present invention, the linker is an amino polyethylene glycol carboxylate of Formula I, or a conjugate linker wherein an amino polyethylene glycol carboxylate of Formula I is conjugated with an amino acid, a dipeptide, a tripeptide or a polypeptide, as defined above, wherein n is 1, 2, 3, 4, 5 or 6, m is 1 and p is 1.

In more preferred aspects of the compounds of the present invention, the linker is an amino polyethylene glycol carboxylate of Formula I, or a conjugate linker wherein an amino polyethylene glycol carboxylate of Formula I is conjugated with an amino acid, a dipeptide, a tripeptide or a polypeptide, as defined above, wherein n is 2, m is 1 and p is 1.

The amino polyethylene glycol carboxylate linker of Formula I, or the conjugate linker wherein an amino polyethylene glycol carboxylate of Formula I is conjugated with an amino acid, a dipeptide, a tripeptide or a polypeptide, as defined above, comprises a small polyethylene glycol moiety (PEG) comprising a structure [—O—CH2-CH2-]$_m$, wherein m is an integer between 1 and 12, (e.g., 1, 2, 3, 4, 5, 6, 7, 8, 9, 10, 11, 12). Such small PEGs are referred to herein as a "mini-PEG". In preferred aspects, the mini-PEG has a structure of Formula I:

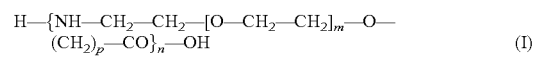

wherein m is any integer from 1 to 12, n is any integer from 1 to 12 and p is 1 or 2. Preferably, the mini-PEG has a structure of Formula I, wherein n is 1, 2, 3, 4, 5 or 6, m is 1 and p is 1. Further preferably, the miniPEG has a structure of Formula I wherein n is 1, m is 1 and p is 1. Suitable reagents for use in acylating an amino acid with a mini-PEG are commercially available from vendors, such as Peptides International (Louisville, Ky.) and ChemPep, Inc. (Wellington, Fla.). Also, suitable techniques for acylating an amino acid with a mini-PEG are described herein (see Examples 1-4).

The mini-PEG of Formula I is a functionalized miniPEG comprising an amine functional group and a carboxyl functional group. The carboxyl functional group reacts with the epsilon-amino group of the lysine side-chain to form an amide bond. The amine functional group reacts with a carboxyl group of the fatty acid. The lysine at position 20 of the peptide of SEQ ID NO: 2 is thus conjugated to a C14-C24 fatty acid via the mini-PEG of Formula I.

Alternatively, when the mini-PEG of Formula I is part of a conjugate linker (i.e. a mini-PEG of Formula I conjugated to an amino acid, a dipeptide, a tripeptide or a polypeptide as defined above), the amine functional group of the mini-PEG of Formula I reacts with a functional group of the amino acid, dipeptide, tripeptide or polypeptide. A further functional group of the amino acid, dipeptide, tripeptide or polypeptide reacts with a carboxyl group of the fatty acid. The lysine at position 20 of the peptide of SEQ ID NO: 2 is thus conjugated to the C14-C24 fatty acid via a conjugate linker as defined above.

The hydrophilic nature of the mini-PEG of Formula I serves to increase the solubility of the compounds of the invention comprising a linker comprising an amino polyethylene glycol carboxylate of Formula I or a conjugate linker wherein an amino polyethylene glycol carboxylate of Formula I is conjugated to an amino acid, a dipeptide, a tripeptide or a polypeptide, as defined.

Preferred linkers comprising a mini-PEG of Formula I include, but are not limited to, ([2-(2-aminoethoxy)-ethoxy]-acetyl)$_2$ and 8-amino-3,6-dioxaoctanoic acid.

The linker may also be a single amino acid positioned between the epsilon-amino group of the lysine side chain and the C14-C24 fatty acid. In some preferred aspects, the amino acid is a hydrophilic amino acid. Suitable amino acids include Arg, Asn, Asp, Gln, Glu, His, Lys, Pro, Ser, Thr, Cit, Orn, Sar, Gly, γ-Abu and γ-Glu.

In more preferred aspects, the amino acid is γ-Glu.

Alternatively, the linker is a dipeptide selected from the group consisting of Ala-Ala, β-Ala-β-Ala, Glu-Glu, Gly-Gly, Leu-Leu, Pro-Pro, Ser-Ser, Thr-Thr, γ-Glu-γ-Glu, Glu-γ-Glu, γ-Glu-Glu, γ-Abu-γ-Abu, 6-aminohexanoic acid-6-aminohexanoic acid, 5-aminovaleric acid-5-aminovaleric acid, 7-aminoheptanoic acid-7-aminoheptanoic acid and 8-aminooctanoic acid-8-aminooctanoic acid.

In a further alternative aspect, each amino acid of the dipeptide can be the same as or different from the other amino acid of the dipeptide, and can be independently selected from the group consisting of Ala, β-Ala, Glu, Gly, Leu, Pro, Ser, Thr, γ-Glu, γ-Abu, 6-aminohexanoic acid, 5-aminovaleric acid, 7-aminoheptanoic acid and 8-aminooctanoic acid.

In more preferred aspects, the linker is γ-Glu-γ-Glu.

In some aspects, the linker is a tripeptide wherein the amino acids of the tripeptide are independently selected from the group consisting of: Ala, β-Ala, Glu, Gly, Leu, Pro, Ser, Thr, γ-aminobutyric acid (γ-Abu), γ-glutamic acid (γ-Glu), 6-aminohexanoic acid, 5-aminovaleric acid, 7-aminoheptanoic acid, and 8-aminooctanoic acid.

In preferred aspects, the linker is a tripeptide selected from the group consisting of Ala-Ala-Ala, β-Ala-β-Ala-β-Ala, Glu-Glu-Glu, γ-Glu-γ-Glu-γ-Glu, Glu-γ-Glu-γ-Glu, γ-Glu-γ-Glu-Glu, γ-Glu-Glu-γ-Glu, Gly-Gly-Gly, Gly-Gly-Ser, Ser-Gly-Gly, Gly-Ser-Gly, Gly-Gly-Glu, Glu-Gly-Gly, Gly-Glu-Gly, Gly-Gly-γ-Glu, γ-Glu-Gly-Gly, Gly-γ-Glu-Gly, Leu-Leu-Leu, Pro-Pro-Pro and γ-Abu-γ-Abu-γ-Abu.

In some aspects, the linker is a polypeptide selected from the group consisting of (Gly-Gly-Ser)$_q$ (Gly-Gly-Gly-Ser)$_r$, and (Gly-Gly-Gly-Gly-Ser)$_r$, (6-aminohexanoic acid)$_s$, (5-aminovaleric acid)$_s$, (7-aminoheptanoic acid)$_s$, and (8-aminooctanoic acid)$_s$, where q is any integer from 2 to 5, r is any integer from 1 to 3, and s is any integer from 4 to 15.

In a preferred aspect, the linker is a conjugate linker wherein an amino polyethylene glycol carboxylate of Formula I:

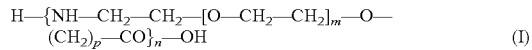

$$\text{H—\{NH—CH}_2\text{—CH}_2\text{—[O—CH}_2\text{—CH}_2]_m\text{—O—(CH}_2)_p\text{—CO\}}_n\text{—OH} \quad \text{(I)}$$

wherein m is any integer from 1 to 12, n is any integer from 1 to 12, and p is 1 or 2, is conjugated with an amino acid, a dipeptide, a tripeptide or a polypeptide, as defined above.

In a preferred aspect, the amino polyethylene glycol carboxylate of the conjugate linker is ([2-(2-aminoethoxy)-ethoxy]-acetyl)$_2$ or 8-amino-3,6-dioxaoctanoic acid.

In a more preferred aspect, the linker comprises ([2-(2-aminoethoxy)-ethoxy]-acetyl)$_2$-(γ-Glu)$_t$ (also referred to as (AEEA)$_2$-(γ-Glu)$_t$), wherein t is 1 or 2. The fatty acid and the gamma-glutamic acid in the linker act as albumin binders, and provide the potential to generate long-acting compounds in vivo. In the most preferred aspects, compounds of the present invention comprise a lysine at position 20 that is chemically modified by conjugation of the epsilon-amino group of the lysine side chain with ([2-(2-aminoethoxy)-ethoxy]-acetyl)$_2$-(γ-Glu)$_t$-CO—(CH$_2$)$_d$—CO$_2$H, wherein t is 1 or 2 and d is 16 or 18.

As shown in the chemical structures of Example 1-4, the first unit of [2-(2-Amino-ethoxy)-ethoxy]-acetyl is linked to the epsilon-amino group of the lysine side-chain. The second unit of [2-(2-Amino-ethoxy)-ethoxy]-acetyl is then attached to the amino-group of the first unit of [2-(2-Amino-ethoxy)-ethoxy]-acetyl. Then, the first unit of γ-Glu is attached to the amino group of the second unit of [2-(2-Amino-ethoxy)-ethoxy]-acetyl through the γ-carboxyl group of the side-chain. When t=2, the second unit of γ-Glu is attached to the α-amino group of the first unit of γ-Glu through the γ-carboxyl group of the side-chain. Finally, the fatty acid is attached to the α-amino group of the first (when t=1) or second (when t=2) unit of γ-Glu.

When the linker is an amino acid, a dipeptide, a tripeptide, or a polypeptide, as defined above, it is preferred that the amino acid, or at least one amino acid of the dipeptide, tripeptide or polypeptide, is a hydrophilic amino acid.

Similarly, when the linker is a conjugate linker wherein an amino polyethylene glycol carboxylate of Formula I:

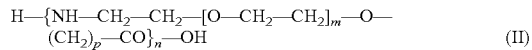

$$\text{H—\{NH—CH}_2\text{—CH}_2\text{—[O—CH}_2\text{—CH}_2]_m\text{—O—(CH}_2)_p\text{—CO\}}_n\text{—OH} \quad \text{(II)}$$

wherein m is any integer from 1 to 12, n is any integer from 1 to 12, and p is 1 or 2; is conjugated with an amino acid, a dipeptide, a tripeptide or a polypeptide, as defined above, it is preferred that the amino acid/at least one amino acid of the amino acid/dipeptide/tripeptide/polypeptide is a hydrophilic amino acid.

Suitable amino acids include, but are not limited to, Arg, Asn, Asp, Gln, Glu, His, Lys, Pro, Ser, Thr, Cit, Orn, Sar, Gly, γ-Abu and γ-Glu.

The present inventors discovered that the presence of one or more hydrophilic amino acids in the linker compensate for a loss of solubility that may normally be expected to occur as a consequence of an amino acid substitution in the peptide of SEQ ID NO: 1. For instance, in the embodiment wherein the linker comprises ([2-(2-aminoethoxy)-ethoxy]-acetyl)$_2$-(γ-Glu)$_t$, wherein t is 1 or 2, Xaa28 of the peptide of SEQ ID NO: 1 can be serine or glutamic acid. The selection of glutamic acid at position 28 of the peptide of SEQ ID NO: 2 improves the solubility of such compounds. The selection of serine at position 28 of the peptide of SEQ ID NO: 2 might be expected to reduce the solubility of such compounds relative to those compounds that differ only by having a glutamic acid residue at position 28. However, a second γ-Glu amino acid in the above-described linker (i.e. t is 2) compensates for this expected reduction in solubility.

The compounds of the present invention utilize a C14-C24 fatty acid chemically conjugated to the epsilon-amino group of a lysine side-chain either by a direct bond or by a linker. The term "C14-C24 fatty acid" as used herein means a carboxylic acid with between 14 and 24 carbon atoms. The C14-C24 fatty acid suitable for use herein can be a saturated monoacid or a saturated diacid. By "saturated" is meant that the fatty acid contains no carbon-carbon double or triple bonds.

Examples of specific saturated C14-C24 fatty acids that are suitable for the compounds and uses thereof disclosed herein include, but are not limited to, myristic acid (tetradecanoic acid)(C14 monoacid), tetradecanedioic acid (C14 diacid), palmitic acid (hexadecanoic acid)(C16 monoacid), hexadecanedioic acid (C16 diacid), margaric acid (heptadecanoic acid)(C17 monoacid), heptadecanedioic acid (C17 diacid), stearic acid (octadecanoic acid)(C18 monoacid), octadecanedioic acid (C18 diacid), nonadecylic acid (nonadecanoic acid)(C19 monoacid), nonadecanedioic acid (C19 diacid), arachadic acid (eicosanoic acid)(C20 monoacid), eicosanedioic acid (C20 diacid), heneicosylic acid (heneicosanoic acid)(C21 monoacid), heneicosanedioic acid (C21 diacid), behenic acid (docosanoic acid)(C22), docosanedioic acid (C22 diacid), lignoceric acid (tetracosanoic acid)(C24 monoacid), tetracosanedioic acid (C24 diacid), including branched and substituted derivatives thereof.

In preferred aspects of the compounds of the present invention, the C14-C24 fatty acid is selected from the group consisting of a saturated C14 monoacid, a saturated C14 diacid, a saturated C16 monoacid, a saturated C16 diacid, a saturated C18 monoacid, a saturated C18 diacid, a saturated C19 diacid, a saturated C20 monoacid, a saturated C20 diacid, a saturated C22 diacid, and branched and substituted derivatives thereof.

In more preferred aspects of the compounds of the present invention, the C14-C24 fatty acid is selected from the group consisting of myristic acid, tetradecanedioic acid, palmitic acid, hexadecanedioic acid, stearic acid, octadecanedioic acid, nonadecanedioic acid, arachadic acid, eicosanedioic acid and docosanedioic acid.

Preferably, the C14-C24 fatty acid is octadecanedioic acid or eicosanedioic acid.

The present inventors have found that the position of the fatty acid is critical in achieving a compound with the desired ratio of Gcg-R/GLP-1-R co-agonist activity. The length and composition of the fatty acid impacts the plasma half-life of the compound, the potency of the compound in in vivo animal models and also impacts the solubility and stability of the compound. Conjugation of the peptide defined in SEQ ID NO: 2 to a C14-C24 saturated fatty monoacid or diacid results in compounds that exhibit desirable plasma half-life, desirable potency in in vivo animal models and also possess desired solubility and stability characteristics. Myristic acid, tetradecanedioic acid, palmitic acid, hexadecanedioic acid, stearic acid, octadecanedioic acid, nonadecanedioic acid, arachadic acid, eicosanedioic acid and docosanedioic acid are particularly preferred fatty acids.

In particular, conjugation of the peptide defined in SEQ ID NO: 2 at the lysine residue at position 20 with octadecanedioic acid or eicosanedioic acid results in compounds that: (i) are capable of achieving the desired ratios of Gcg-R/GLP-1-R co-agonist activity, (ii) are capable of improving potency in in vivo animal models and/or (iii) are capable of improving physical stability and solubility characteristics.

The compounds of the invention are preferably formulated as pharmaceutical compositions administered by parenteral routes (e.g., subcutaneous, intravenous, intraperitoneal, intramuscular, or transdermal).

The compounds of the present invention typically will be administered parenterally. Parenteral administration includes, for example, systemic administration, such as by intramuscular, intravenous, subcutaneous, intradermal, or intraperitoneal injection. The preferred route of administration is subcutaneous injection. A compound of the present invention is administered to the subject in conjunction with an acceptable pharmaceutical carrier, diluent, or excipient as part of a pharmaceutical composition for treating type 2 diabetes, obesity, NAFLD and/or NASH. The pharmaceutical composition can be a solution or a suspension such as one in which a compound of the present invention is complexed with a divalent metal cation such as zinc. A compound of the present invention may also be formulated in a solid formulation such as by lyophilization or spray drying, which is then reconstituted in a suitable diluent solution prior to administration. Suitable pharmaceutical carriers may contain inert ingredients which do not interact with the peptide or peptide derivative. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Some examples of suitable excipients include lactose, dextrose, sucrose, trehalose, sorbitol, and mannitol and preservatives such as phenol and m-cresol.

Standard pharmaceutical formulation techniques, such as those described in Remington: The Science and Practice of Pharmacy (D. B. Troy, Editor, 21st Edition, Lippincott, Williams & Wilkins, 2006), may be employed. The compounds of the present invention may alternatively be formulated for administration through the buccal, oral, transdermal, nasal, or pulmonary route.

The compounds of the present invention may react with any of a number of inorganic and organic acids to form pharmaceutically acceptable acid addition salts. Pharmaceutically acceptable salts and common methodology for preparing them are well known in the art. See, e.g., P. Stahl, et al. Handbook of Pharmaceutical Salts: Properties, Selection and Use, 2nd Revised Edition (Wiley-VCH, 2011). Pharmaceutically acceptable salts of the present invention include trifluoroacetate, hydrochloride, and acetate salts.

The compounds of the present invention may be employed to treat diabetes, specifically type 2 diabetes. Additional subjects who may benefit from treatment with the compounds of the present invention, include those with impaired glucose tolerance or impaired fasting glucose, subjects whose body weight is about 25% or more above normal body weight for the subject's height and body build, subjects having one or more parents with type 2 diabetes, subjects who have had gestational diabetes, and subjects with metabolic disorders such as those resulting from decreased endogenous insulin secretion. The compounds of the present invention may be used to prevent subjects with impaired glucose tolerance from proceeding to develop type 2 diabetes, prevent pancreatic β-cell deterioration, induce β-cell proliferation, improve β-cell function, activate dormant β-cells, promote differentiation of cells into β-cells, stimulate β-cell replication, and inhibit β-cell apoptosis. Other diseases and conditions that may be treated or prevented using compounds of the invention in methods of the invention include: Maturity-Onset Diabetes of the Young (MODY) (Herman, et al., *Diabetes* 43:40, 1994); Latent Autoimmune Diabetes Adult (LADA) (Zimmet, et al., *Diabetes Med.* 11:299, 1994); impaired glucose tolerance (IGT) (Expert Committee on Classification of Diabetes Mellitus, *Diabetes Care* 22 (Supp. 1):S5, 1999); impaired fasting glucose (IFG) (Charles, et al., *Diabetes* 40:796, 1991); gestational diabetes (Metzger, *Diabetes,* 40:197, 1991); metabolic syndrome X, dyslipidemia, hyperglycaemia, hyperinsulinemia, hypertriglyceridemia, and insulin resistance.

The compounds of the invention may also be used in methods of the invention to treat secondary causes of diabetes (Expert Committee on Classification of Diabetes Mellitus, *Diabetes Care* 22 (Supp. 1):S5, 1999). Such secondary causes include glucocorticoid excess, growth hormone excess, pheochromocytoma, and drug-induced diabetes. Drugs that may induce diabetes include, but are not limited to, pyriminil, nicotinic acid, glucocorticoids, phenytoin, thyroid hormone, β-adrenergic agents, α-interferon and drugs used to treat HIV infection.

The compounds of the present invention may be effective in the suppression of food intake and the treatment of obesity.

An "effective amount" of a compound of the present invention is the quantity that results in a desired therapeutic and/or prophylactic effect without causing unacceptable side effects when administered to a subject. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment. For example, an "effective amount" of a compound of the present invention for the treatment of T2D is the quantity that would result in greater control of blood glucose concentration than in the absence of treatment, thereby resulting in a delay in the onset of diabetic complications such as retinopathy, neuropathy, or kidney disease. An "effective amount" of a compound of the present invention for the prevention of type 2 diabetes, for example in subjects with impaired glucose tolerance or impaired fasting glucose, is the quantity that would delay, compared with the absence of treatment, the onset of elevated blood glucose levels that require treatment with anti-hyperglycaemic drugs such as sulfonylureas, thiazolidinediones, insulin, and/or bisguanidines.

An "effective amount" of a compound of the present invention administered to a subject will also depend on the type and severity of the disease and on the characteristics of the subject, such as general health, age, sex, body weight and tolerance to drugs. The dose of a compound of the present invention effective to normalize a subject's blood glucose will depend on a number of factors, among which are included, without limitation, the subject's sex, weight and age, the severity of inability to regulate blood glucose, the route of administration and bioavailability, the pharmacokinetic profile of the peptide, the potency, and the formulation.

Certain compounds of the present invention are generally effective over a wide dosage range. For example, dosages for once-weekly dosing may fall within the range of about 0.05 to about 30 mg per person per week. Certain compounds of the present invention may be dosed daily. Additionally, certain compounds of the present invention may be dosed bi-weekly, once-weekly or monthly.

A "subject" is a mammal, preferably a human, but can also be an animal, including companion animals (e.g., dogs, cats, and the like), farm animals (e.g., cows, sheep, pigs, horses, and the like) and laboratory animals (e.g., rats, mice, guinea pigs, and the like).

As used herein, the term "treating" or "to treat" includes restraining, slowing, stopping, or reversing the progression or severity of an existing symptom or disorder.

The term "plasma half-life" refers to the time required for half of the relevant compounds to be cleared from the plasma. An alternatively used term is "elimination half-life". The term "extended" or "longer" used in the context of plasma half-life or elimination half-life indicates that there is a significant increase in the half-life of a compound of the present invention relative to that of the reference molecule (e.g. non-fatty acid-conjugated form of the peptide, wild type human OXM or semaglutide) as determined under comparable conditions.

Clearance is a measure of the body's ability to eliminate a drug from circulation. As clearance decreases due, for example, to modifications to a drug, half-life would be expected to increase. However, this reciprocal relationship is exact only when there is no change in the volume of distribution. A useful approximate relationship between the terminal log-liner half-life ($T_{1/2}$), clearance (C) and volume of distribution (V) is given by the equation: $T_{1/2} \approx 0.693$ (V/C). Clearance does not indicate how much drug is being removed but, rather, the volume of biological fluid such as blood or plasma that would have to be completely freed of drug to account for the elimination. Clearance is expressed as a volume per unit of time.

As used herein, the term "hydrophilic" refers to the property of being able to readily absorb moisture and having strongly polar groups that readily interact with water.

As used herein, "semaglutide" refers to a chemically synthesized GLP-1 analogue that has the peptide backbone and overall compound structure of that found in CAS Registry Number 910463-68-2.

The amino acid sequences of the present invention contain the standard single letter or three letter codes for the twenty naturally occurring amino acids. Additionally, "Aib" is alpha amino isobutyric acid, "Abu" is aminobutyric acid, "Orn" is ornithine, "Cit" is citrulline and "Sar" is sarcosine.

As used herein, the term "C-terminal amino acid" refers to the last amino acid in the sequence of a peptide that contains a free carboxyl group. The C-terminal amino acid of the compounds of the present invention is Gly at position 34.

The present invention also encompasses novel intermediates and processes useful for the synthesis of compounds of the present invention, or a pharmaceutically acceptable salt thereof. The intermediates and compounds of the present invention may be prepared by a variety of procedures known in the art. In particular, the process using chemical synthesis is illustrated in the Examples below. The specific synthetic steps for each of the routes described may be combined in different ways to prepare compounds of the present invention, or salts thereof. The reagents and starting materials are readily available to one of ordinary skill in the art. It is understood that these Examples are not intended to be limiting to the scope of the invention in any way.

EXAMPLE 1

HXaa2QGTFTSDYSKYLDEKKAKEFVEWLLEGGPSSG wherein Xaa2 is Aib;

K at position 20 is chemically modified through conjugation to the epsilon-amino group of the K side-chain with ([2-(2-Amino-ethoxy)-ethoxy]-acetyl)$_2$-(γGlu)$_1$-CO—(CH$_2$)$_{16}$—CO$_2$H; and the C-terminal amino acid is amidated as a C-terminal primary amide (SEQ ID NO: 5).

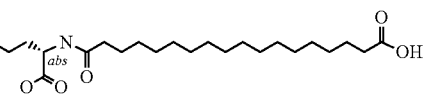

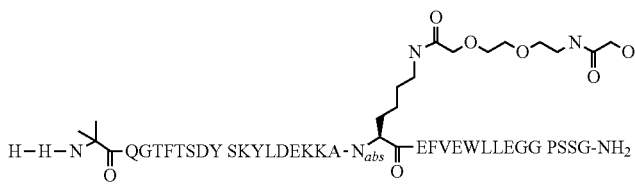

The above diagram depicts the structure of the compound of SEQ ID NO: 5 (hereinafter referred to as "Compound 1") using the standard single letter amino acid code with the exception of residues Aib2 and K20 where the structures of these amino acids have been expanded.

The peptide component of Compound 1 is synthesized by automated solid-phase synthesis using Fluorenylmethyloxy-carbonyl (Fmoc)/tert-Butyl (t-Bu) chemistry on a Symphony 12-channel multiplex peptide synthesizer (Protein Technologies, Inc. Tucson, Ariz.).

The synthesis resin consists of 1% DVB cross-linked polystyrene (Fmoc-Rink-MBHA Low Loading resin, 100-200 mesh, EMD Millipore, Temecula, Calif.) at a substitution 0.3-0.4 meq/g. Standard side-chain protecting groups are as follows: tert-butyloxycarbonyl (Boc) for Trp and Lys; tert-butyl ester (OtBu) for Asp and Glu; tBu for Ser, Thr and Tyr; and triphenylmethyl (Trt) for Gln; N-α-Fmoc-N-ε-4-methyltrityl-L-lysine (Fmoc-Lys(Mtt)-OH) was used for the lysine at position 20 of SEQ ID NO: 3 and $N_\alpha,N_{(im)}$-di-Boc-L-histidine (Boc-His(Boc)-OH) was used for the histidine at position 1. Fmoc groups were removed prior to each coupling step (2×7 minutes) using 20% piperidine in dimethylformamide (DMF). All standard amino acid couplings are performed for 1 hour, using an equal molar ratio of Fmoc amino acid (EMD Millipore, Temecula, Calif.), diisopropylcarbodiimide (DIC)(Sigma-Aldrich, St. Louis, Mo.) and Oxyma (Oxyma Pure, Iris Biotech, Marktredwitz, Germany), at a 9-fold molar excess over the theoretical peptide loading and at a final concentration of 0.18 M in DMF.

Two exceptions are the glutamine residue at position 3 of SEQ ID NO: 5, which is double-coupled (2×1 hour), and the histidine residue at position 1 of SEQ ID NO: 5, which was coupled at a 6-fold molar excess using 1-Hydroxy-7-azabenzotriazole (HOAt) instead of Oxyma for 18 hours. After completion of the synthesis of the linear peptide, the resin was transferred to a disposable fritted 25 mL polypropylene syringe (Torviq, Niles, Mich.) equipped with a polytetrafluoroethylene (PTFE) stopcock (Biotage, Charlotte, N.C.) and the 4-Methyltrityl (Mtt) protecting group on the lysine at position 20 of SEQ ID NO: 5 was selectively removed from the peptide resin using three treatments with 20% hexafluoroisopropanol (Oakwood Chemicals, West Columbia, S.C.) in DCM (2×10 minutes and 1×45 minutes) to expose the free epsilon amine of the lysine at position 20 and make it available for further reaction.

Subsequent attachment of the fatty acid-linker moiety is accomplished by performing two succeeding couplings of [2-(2-(Fmoc-amino)ethoxy)ethoxy]acetic acid (Fmoc-AEEA-OH) (ChemPep, Inc. Wellington, Fla.; 3-fold excess of amino acid (AA):1-[Bis(dimethylamino)methylene]-1H-1,2,3-triazolo[4,5-b]pyridinium-3-oxid hexafluorophosphate (HATU): N,N-diisopropylethylamine (DIPEA) [1:1:5 mol/mol] for a 3 hour coupling time), followed by coupling of Fmoc-glutamic acid α-t-butyl ester (Fmoc-Glu-OtBu) (Ark Pharm, Inc. Libertyville Ill., 3-fold excess of AA:HATU:DIPEA [1:1:5 mol/mol] for a 3 hour coupling time). In each case, the Fmoc moiety is removed as described above. Finally, mono-OtBu-octadecanedioic acid (WuXi AppTec, Shanghai, China) is coupled to the resin over 18 hours using a 3-fold excess of acid:HATU:DIPEA (1:1:5 mol/mol).

After the synthesis is complete, the peptide resin is washed with dichloromethane (DCM), diethyl ether and thoroughly air dried by applying vacuum suction to the syringe for 5 minutes. The dry resin is treated with a cleavage cocktail (trifluoroacetic acid (TFA): anisole: water: triisopropylsilane, 88:5:5:2 v/v) for 2 hours at room temperature to release the peptide from the solid support and remove all side-chain protecting groups. The resin is filtered off, washed twice with neat TFA, and the combined filtrates are treated with cold diethyl ether to precipitate the crude peptide. The peptide/ether suspension is then centrifuged at 4000 rpm to form a solid pellet, the supernatant is decanted, and the solid pellet is triturated with ether two additional times and dried in vacuo. The crude peptide is solubilized in 20% acetonitrile/water and purified by RP-HPLC on a C8 preparative column (Luna 21×250 mm, Phenomenex, Torrance, Calif.) with linear gradients of acetonitrile and water using three different buffer systems:

1) 0.1 M ammonium acetate in water, pH 5.0;
2) 0.1% TFA in water; and
3) 5% acetic acid in water.

Subsequent lyophilization of the final main product pool yields the lyophilized peptide acetate salt.

In a synthesis performed essentially as described above, the purity of Compound 1 is assessed using analytical RP-HPLC and found to be >97%.

The molecular weight is determined by analytical electrospray MS. The molecular weight of Compound 1 is calculated to be 4535.0 Daltons while the observed deconvoluted averaged molecular weight was determined to be 4535.0 Daltons and the following ions were observed: 1512.3 (M+3H), 1134.3 (M+4H), 908 (M+5H).

EXAMPLE 2

HXaa2QGTFTSDYSKYLDEKKAKEFVEWLLEGGPSSG wherein Xaa2 is Aib;

K at position 20 is chemically modified through conjugation to the epsilon-amino group of the K side-chain with ([2-(2-Amino-ethoxy)-ethoxy]-acetyl)$_2$-(γGlu)$_1$-CO—(CH$_2$)$_{18}$—CO$_2$H; and the C-terminal amino acid is amidated as a C-terminal primary amide (SEQ ID NO: 6).

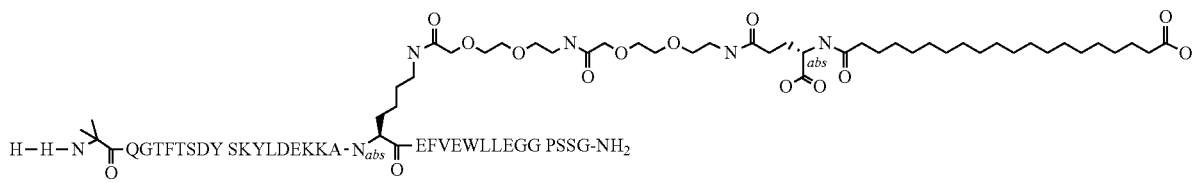

The above diagram depicts the structure of the compound of SEQ ID NO: 6 (hereinafter referred to as "Compound 2") using the standard single letter amino acid code with the exception of residues Aib2 and K20 where the structures of these amino acids have been expanded.

Compound 2 is synthesized as in Example 1, except that mono-OtBu-eicosanedioic acid (WuXi AppTec, Shanghai, China) is coupled to the resin over 18 hours using a 3-fold excess of AA:HATU:DIPEA (1:1:5 mol/mol), rather than mono-OtBu-octadecanedioic acid as in Example 1.

The molecular weight of Compound 2 is calculated to be 4563.1 Daltons while the observed deconvoluted averaged molecular weight is determined to be 4562.9 Daltons and the following ions were observed: 1521.7 (M+3H), 1141.3 (M+4H), 913.5 (M+5H).

EXAMPLE 3

HXaa2QGTFTSDYSKYLDEKKAKEFVEWLLSGGPSSG wherein Xaa2 is Aib;
K at position 20 is chemically modified through conjugation to the epsilon-amino group of the K side-chain with ([2-(2-Amino-ethoxy)-ethoxy]-acetyl)$_2$-($\gamma$Glu)$_2$-CO—(CH$_2$)$_{16}$—CO$_2$H; and
the C-terminal amino acid is amidated as a C-terminal primary amide (SEQ ID NO: 7).

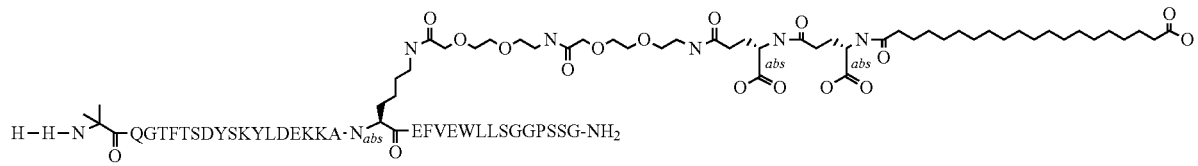

The above diagram depicts the structure of the compound of SEQ ID NO: 7 (hereinafter referred to as "Compound 3") using the standard single letter amino acid code with the exception of residues Aib2 and K20 where the structures of these amino acids have been expanded.

Compound 3 is synthesized as in Example 1, except that an additional Fmoc-Glu-OtBu moiety was added in the linker synthesis cycle.

The molecular weight of Compound 3 is calculated to be 4622.1 Daltons while the observed deconvoluted averaged molecular weight was determined to be 4621.9 Daltons and the following ions were observed: 1541.3 (M+3H), 1156.2 (M+4H), 925.2 (M+5H).

EXAMPLE 4

HXaa2QGTFTSDYSKYLDEKKAKEFVEWLLSGGPSSG wherein Xaa2 is Aib;
K at position 20 is chemically modified through conjugation to the epsilon-amino group of the K side-chain with ([2-(2-Amino-ethoxy)-ethoxy]-acetyl)$_2$-($\gamma$Glu)$_2$-CO—(CH$_2$)$_{18}$—CO$_2$H; and
the C-terminal amino acid is amidated as a C-terminal primary amide (SEQ ID NO: 8).

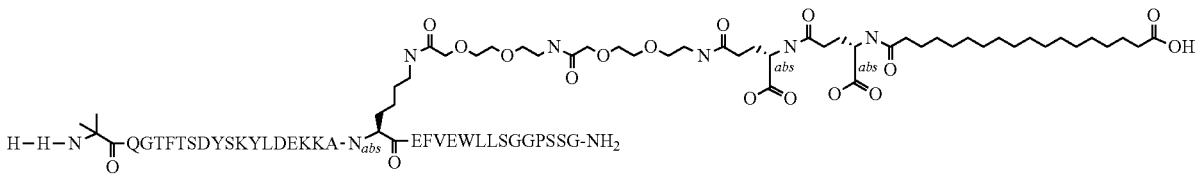

The above diagram depicts the structure of the compound of SEQ ID NO: 8 (hereinafter referred to as "Compound 4") using the standard single letter amino acid code with the exception of residues Aib2 and K20 where the structures of these amino acids have been expanded.

Compound 4 is synthesized as in Example 1, except that mono-OtBu-eicosanedioic acid (WuXi AppTec, Shanghai, China) is coupled to the resin over 18 hours using a 3-fold excess of AA:HATU:DIPEA (1:1:5 mol/mol), rather than mono-OtBu-octadecanedioic acid used in Example 1. In addition, an additional amino acid Fmoc-Glu-OtBu moiety is added in the linker synthesis cycle.

The molecular weight of the peptide is calculated to be 4650.1 Daltons while the observed deconvoluted averaged molecular weight is determined to be 4650.1 Daltons and the following ions were observed: 1550.7 (M+3H), 1163.3 (M+4H), 930.8 (M+5H).

Physical Characteristics

Viscosity

Viscosity of compounds of the present invention is measured in a Rheosense mVroc Viscometer with the following settings:
(a) Syringe size: 500 µL syringe
(b) Flow Rate: 100 µL/min flow rate
(c) Average Temperature: 25° C.
(d) Shear Rate: 1934 s$^{-1}$ Dry powder (compound) is weighed out, dissolved in water as a cloudy precipitate, and titrated to approximately pH 8.0 with 1N NaOH. The solution is sonicated and swirled by hand until peptide is in solution. Samples are sterile filtered (0.22 µm PVDF filters). Samples are then analyzed by UV-Vis to assess stock solution concentrations. Solutions are diluted to final concentration using 3× m-cresol in 10 mM Tris pH 8.0 buffer to final concentrations of approximately 10 mg/mL peptide by weight in 10 mM Tris+3 mg/mL m-cresol at pH 8.0. Samples were filtered through 0.22 µm filters immediately prior to viscosity analysis. 25 µL of sample are removed to verify concentration by RP-HPLC before and after analysis.

Water and buffer control samples are measured before and after each sample is analyzed. The instrument is washed with buffer (3×) in between analysis of each sample. The samples are loaded into individual syringes and analyzed. The first measurement is not included in the final calculation to allow for equilibration with the system. Samples are then analyzed in triplicate (n=3).

The viscosity of Compounds 1-4 was measured essentially as described in this assay. The viscosity data for Compounds 1-4 is summarized in Table 1.

TABLE 1

Viscosity data for Compounds 1-4

| Sample | 500 µL syringe Viscosity (cP or mPa-s) |
|---|---|
| Buffer Control | 0.99 |
| Compound 1 | 1.06 |
| Compound 2 | 1.04 |
| Compound 3 | 1.03 |
| Compound 4 | 1.05 |

Solubility

Solubility of compounds of the present invention is measured in an Agilent 1100 HPLC, an Agilent 1200 HPLC and a Nanodrop 2000. The following HPLC columns are used:
(a) RP-HPLC: Waters Symmetry Shield C18, 3.6 um, 4.6× 100 mm
(b) HPLC-SEC: Tosoh Biosciences, TSK2000$_{SWXL}$ 7.8 cm×30 mm All peptide concentrations are made at 10 mg/mL in the following:
(a) 10 mM Tris pH 8.0+3 mg/mL m-cresol
(b) 10 mM Tris pH 8.0+3 mg/mL m-cresol+150 mM NaCl
(c) 10 mM Tris pH 8.0+3 mg/mL m-cresol+0.02% Tween-20
(d) PBS pH 7.4

5 mL of 10 mg/mL peptide dissolved in 10 mM Tris at pH 8.0 is concentrated to approximately 20 mg/mL using Amicon-ultra 3 kDa MWCO devices. The solution is filtered using Millivex 0.22 µM filters (PVDF membrane) and the final concentration is measured by the NanoDrop spectrometer. This stock solution is used to formulate to the final conditions stated above using 3× m-cresol, 10× NaCl, and 100× Tween-20 stock solutions. A 10 mg/mL PBS solution is also prepared by dissolving directly at 5 mg/mL and concentrating using Amicon-ultra 3 kDa MWCO devices.

Each solution is placed in a refrigerator at 4° C. for 1 week, with analysis by RP-HPLC to assess concentration and HPLC-SEC to assess HMW species formation. Analyses completed at T-0 week and T-1 week.

The solubility of Compounds 1-4 was measured essentially as described in this assay. The solubility data for Compounds 1-4 is summarized in Tables 2(a)-(d).

TABLE 2(a)

Solubility data for Compound 1

| PARAMETER | SUMMARY |
|---|---|
| Solubility/ Dissolution | 10 mg/mL solubility in Tris pH 8 + 3 mg/mL m-cresol (T8m); 10 mg/mL solubility in Tris pH 8 + 3 mg/mL m-cresol + 150 mm NaCl (T8Nm); 10 mg/mL solubility in Tris pH 8 + 3 mg/mL m-cresol + 0.02% Tween-20(T8Tm); 10 mg/mL solubility in PBS, pH 7.4; No visible precipitation or phase separation observed after 1 week storage at 4° C.; No observed HMW species formation by SEC-HPLC; RP-HPLC verifies 10 mg/mL concentration maintained over course of 1 week study. |

TABLE 2(b)

Solubility data for Compound 2

| PARAMETER | SUMMARY |
|---|---|
| Solubility/ Dissolution | 10 mg/mL solubility in Tris pH 8 + 3 mg/mL m-cresol (T8m); 10 mg/mL solubility in Tris pH 8 + 3 mg/mL m-cresol + 150 mm NaCl (T8Nm); 10 mg/mL solubility in Tris pH 8 + 3 mg/mL m-cresol + 0.02% Tween-20(T8Tm); |

TABLE 2(b)-continued

Solubility data for Compound 2

| PARAMETER | SUMMARY |
|---|---|
| | 10 mg/mL solubility in PBS, pH 7.4;<br>No visible precipitation or phase separation observed after 1 week storage at 4° C.;<br>No observed HMW species formation by SEC-HPLC;<br>RP-HPLC verifies 10 mg/mL concentration maintained over course of 1 week study |

TABLE 2(c)

Solubility data for Compound 3

| PARAMETER | SUMMARY |
|---|---|
| Solubility/<br>Dissolution | 10 mg/mL solubility in Tris pH 8 + 3 mg/mL m-cresol (T8m);<br>10 mg/mL solubility in Tris pH 8 + 3 mg/mL m-cresol + 150 mm NaCl (T8Nm);<br>10 mg/mL solubility in Tris pH 8 + 3 mg/mL m-cresol + 0.02% Tween-20(T8Tm);<br>10 mg/mL solubility in PBS, pH 7.4;<br>No visible precipitation or phase separation observed after 1 week storage at 4° C.;<br>No observed HMW species formation by SEC-HPLC;<br>RP-HPLC verifies 10 mg/mL concentration maintained over course of 1 week study. |

TABLE 2(d)

Solubility data for Compound 4

| PARAMETER | SUMMARY |
|---|---|
| Solubility/<br>Dissolution | 10 mg/mL solubility in Tris pH 8 + 3 mg/mL m-cresol (T8m);<br>10 mg/mL solubility in Tris pH 8 + 3 mg/mL m-cresol + 150 mm NaCl (T8Nm);<br>10 mg/mL solubility in Tris pH 8 + 3 mg/mL m-cresol + 0.02% Tween-20(T8Tm);<br>10 mg/mL solubility in PBS, pH 7.4;<br>No visible precipitation or phase separation observed after 1 week storage at 4° C.;<br>No observed HMW species formation by SEC-HPLC;<br>RP-HPLC verifies 10 mg/mL concentration maintained over course of 1 week study. |

In Vitro Function

Binding Affinity of Compounds 1-4 for Recombinant Human Gcg Receptor (hGcg-R) and Human GLP-1 Receptor (hGLP-1-R)

Radioligand competition binding assays using scintillation proximity assay (SPA) methods and membranes prepared from 293HEK stably transfected cells overexpressing hGcg-R or hGLP-1-R were run to determine equilibrium dissociation constants (KO for Compounds 1-4. The experimental protocols and results are described below.

hGLP-1R Binding Assay

The GLP-1 receptor binding assay uses cloned hGLP-1-R (Graziano M P, Hey P J, Borkowski D, Chicchi G G, Strader C D, Biochem Biophys Res Commun. 196(1): 141-6, 1993) isolated from 293HEK cells overexpressing recombinant hGLP-1R. The hGLP-1R cDNA is subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5:1189-1192, 1987). This plasmid DNA is transfected into 293HEK cells and selected with 200 µg/mL Hygromycin.

Crude plasma membranes are prepared using cells from adherent culture. The cells are lysed on ice in hypotonic buffer containing 50 mM Tris HCl, pH 7.5 and Roche Complete™ Protease Inhibitors with EDTA. The cell suspension is disrupted using a glass Potter-Elvehjem homogenizer fitted with a Teflon® pestle for 25 strokes. The homogenate is centrifuged at 4° C. at 1100× g for 10 minutes. The supernatant is collected and stored on ice while the pellet is resuspended in hypotonic buffer and rehomogenized. The mixture is centrifuged at 1100×g for 10 minutes. The second supernatant is combined with the first supernatant and centrifuged at 35000×g for 1 hour at 4° C. The membrane pellet is resuspended in homogenization buffer containing protease inhibitors, quick frozen in liquid nitrogen and stored as aliquots in a −80° C. freezer until use.

GLP-1 is radioiodinated by the I-125-lactoperoxidase procedure and purified by reversed phase HPLC at Perkin-Elmer (NEX308). The specific activity is 2200 Ci/mmol $K_D$ determination is performed by homologous competition instead of saturation binding due to high propanol content in the 1-125 GLP-1 material. The $K_D$ is estimated to be 1.24 nM and is used to calculate $K_i$ values for all compounds tested.

The receptor binding assay is carried out using a Scintillation Proximity Assay (SPA) format with wheat germ agglutinin (WGA) beads (Perkin Elmer). The binding buffer contains 25 mM 4-(2-hydroxyethyl)-1-piperazineethanesulfonic acid (HEPES), pH 7.4, 2.5 mM $CaCl_2$, 1 mM $MgCl_2$, 0.1% (w/v) bacitracin (Affymetrix), 0.003% (w/v) Polyoxyethylenesorbitan monolaurate (TWEEN®-20) and Roche Complete™ Protease Inhibitors without EDTA. GLP-1 is dissolved in DMSO at 0.339 mg/mL (0.1 mM) and stored frozen at −20° C. in 100 µL aliquots. The GLP-1 aliquot is diluted and used in binding assays within an hour. The peptide analogue is dissolved in dimethyl sulfoxide (DMSO) and 3-fold serially diluted in 100% DMSO. Next, 5 µL serially diluted compound or DMSO is transferred into Corning® 3632 clear bottom assay plates containing 45 µL assay binding buffer or unlabeled GLP-1 control (non-specific binding (NSB) at 0.25 µM final). Then, 50 µL hGLP-1R membranes (0.5 µg/well), 50 µL 1-125 GLP-1 (0.15 nM final), and 50 µL of WGA beads (150 µg/well) are added, plates are sealed and mixed on a plate shaker (setting 6) for 1 minute. Plates are read with a PerkinElmer Trilux MicroBeta® scintillation counter after 12 hours of settling time at room temperature.

Results are calculated as a percent of specific I-125-GLP-1 binding in the presence of compound. The Absolute $IC_{50}$ concentration of compound is derived by non-linear regression of percent specific binding of I-125-GLP-1 vs. the concentration of compound added. The $IC_{50}$ concentration is converted to $K_i$ using the Cheng-Prusoff equation (Cheng, Y., Prusoff, W. H., Biochem. Pharmacol. 22, 3099-3108, (1973)).

The $K_i$ of Compounds 1-4, human Gcg and human GLP-1(7-36)$NH_2$ at the hGLP-1-R are shown in Table 3 below. The number of replicates (n) is indicated in parenthesis. A (>) qualifier indicates that % inhibition did not reach 50% and the calculated $K_i$ is obtained using the highest concentration tested. n=1/n indicates that the averages are not calculated when all the values have a > sign and the value shown is the highest calculated value.

TABLE 3

$K_i$ of Compounds 1-4, human Gcg and human GLP-1(7-36)$NH_2$ at the hGLP-1-R

| Compound | $K_i$, nM ± SEM, (n) |
| --- | --- |
| Compound 1 | 23.0 ± 5.5 (n = 6) |
| Compound 2 | 28.6 ± 4.8 (n = 4) |
| Compound 3 | 8.68 ± 1.60 (n = 4) |
| Compound 4 | 20.2 ± 8.2 (n = 4) |
| Human Gcg | >4940 (n = 1/2) |
| Human GLP-1 (7-36)$NH_2$ | 0.75 ± 0.056 (n = 67) | hGcg-R Binding Assay

The Gcg receptor binding assay utilizes cloned hGcg-R (Lok, S, et. al., Gene 140 (2), 203-209 (1994)) isolated from 293HEK cells overexpressing the recombinant hGcg-R. The hGcg-R cDNA is subcloned into the expression plasmid phD (Trans-activated expression of fully gamma-carboxylated recombinant human protein C, an antithrombotic factor. Grinnell, B. W., et. al., Bio/Technology 5: 1189-1192 (1987)). This plasmid DNA is transfected into 293HEK cells and selected with 200 µg/mL Hygromycin.

Crude plasma membranes are prepared using cells from adherent culture. The cells are lysed on ice in hypotonic buffer containing 50 mM Tris HCl, pH 7.5 and Roche Complete™ Protease Inhibitors with EDTA. The cell suspension is disrupted using a glass Potter-Elvehjem homogenizer fitted with a Teflon® pestle for 25 strokes. The homogenate is centrifuged at 4° C. at 1100× g for 10 minutes. The supernatant is collected and stored on ice while the pellet is resuspended in hypotonic buffer and rehomogenized. The mixture is centrifuged at 1100×g for 10 minutes. The second supernatant is combined with the first supernatant and centrifuged at 35000×g for 1 hour at 4° C. The membrane pellet is resuspended in homogenization buffer containing protease inhibitors, quick frozen in liquid nitrogen and stored as aliquots in a −80° C. freezer until use.

Gcg is radioiodinated by I-125-lactoperoxidase procedure and purified by reversed phase HPLC at Perkin-Elmer (NEX207). The specific activity is 2200 Ci/mmol $K_D$ determination is performed by homologous competition instead of saturation binding due to high propanol content in the 1-125 Gcg material. The $K_D$ is estimated to be 3.92 nM and is used to calculate $K_i$ values for all compounds tested.

The receptor binding assay is carried out using a Scintillation Proximity Assay (SPA) format with wheat germ agglutinin (WGA) beads (Perkin Elmer). The binding buffer contains 25 mM HEPES, pH 7.4, 2.5 mM $CaCl_2$, 1 mM $MgCl_2$, 0.1% (w/v) bacitracin (Affymetrix), 0.003% (w/v) Polyoxyethylenesorbitan monolaurate (TWEEN®-20) and Roche Complete™ Protease Inhibitors without EDTA. Gcg is dissolved in DMSO at 3.48 mg/mL (1 mM) and stored frozen at −20° C. in 100 µL aliquots. The Gcg aliquot is diluted and used in binding assays within an hour. The peptide analog is dissolved in DMSO and 3-fold serially diluted in 100% DMSO. Next, 5 µL serially diluted compound or DMSO is transferred into Corning® 3632 clear bottom assay plates containing 45 µL assay binding buffer or unlabeled Gcg control (NSB at 1 µM final). Then, 50 µL hGcg-R membranes (0.5 µg/well), 50 µL 1-125 Gcg (0.15 nM final in reaction), and 50 µL of WGA beads (150 µg/well) are added, plates sealed and mixed on a plate shaker (setting 6) for 1 minute. Plates are read with a PerkinElmer Trilux MicroBeta® scintillation counter after 12 hours of settling time at room temperature.

Results are calculated as a percent of specific I-125-Gcg binding in the presence of compound. The Absolute $IC_{50}$ concentration of compound is derived by non-linear regression of percent specific binding of I-125-Gcg vs. the concentration of compound added. The $IC_{50}$ concentration is converted to $K_i$ using the Cheng-Prusoff equation) Cheng, Y., Prusoff, W. H., Biochem. Pharmacol. 22, 3099-3108, (1973)). The $K_i$ of Compounds 1-4, human Gcg and human GLP-1(7-36)$NH_2$ at the hGcg-R are shown in Table 4 below. The number of replicates (n) is indicated in parenthesis. A (>) qualifier indicates that % inhibition did not reach 50% and the calculated $K_i$ is obtained using the highest concentration tested. n=½ indicates that the averages are not calculated when all the values have a > sign and the result value shown is the highest calculated value.

TABLE 4

$K_i$ of Compounds 1-4, human Gcg and human GLP-1(7-36)$NH_2$ at the hGcg-R

| Compound | $K_i$, nM ± SEM, (n) |
| --- | --- |
| Compound 1 | 14.6 ± 4.4 (n = 6) |
| Compound 2 | 17.7 ± 5.0 (n = 4) |
| Compound 3 | 37.3 ± 4.2 (n = 4) |
| Compound 4 | 27.4 ± 3.3 (n = 4) |
| Human Gcg | 2.49 ± 0.24 (n = 73) |
| Human GLP-1(7-36)$NH_2$ | >2420 (n = 1/2) |

Functional hGLP-1-R and hGcg-R Assays

Functional activity is determined in hGLP-1-R and hGcg-R expressing HEK-293 clonal cell lines. The experimental protocols and results are described below.

Each receptor over-expressing cell line is treated with peptide in DMEM (Dulbecco's Modified Eagle Medium, Gibco Cat#31053) supplemented with 1× GlutaMAX™ (L-alanyl-L-glutamine dipeptide in 0.85% NaCl, Gibco Cat#35050), 0.25% FBS (dialyzed fetal bovine serum, Gibco Cat#26400), 0.05% fraction V BSA (bovine albumin fraction V, Gibco Cat#15260), 250 μM IBMX (3-Isobutyl-1-methylxanthine) and 20 mM HEPES [N-(2-Hydroxyethyl) piperazine-N'-(2-ethanesulfonic acid), HyClone Cat# SH30237.01] in a 40 μl assay volume. After a 60 minute incubation at room temperature, the resulting increase in intracellular cAMP (adenosine 3',5'-cyclic monophosphate) is quantitatively determined using the CisBio cAMP Dynamic 2 HTRF Assay Kit (62AM4PEJ). cAMP levels within the cell are detected by adding the cAMP-d2 conjugate in cell lysis buffer (20 μl) followed by the antibody anti-cAMP-Eu$^{3+}$-Cryptate, also in cell lysis buffer (20 μl). The resulting competitive assay is incubated for at least 60 min at room temperature, then detected using a PerkinElmer Envision® instrument with excitation at 320 nm and emission at 665 nm and 620 nm. Envision units (emission at 665 nm/620 nm*10,000) are inversely proportional to the amount of cAMP present and are converted to nM cAMP per well using a cAMP standard curve. The amount of cAMP generated (nM) in each well is converted to a percent of the maximal response observed with either 10 nM human GLP-1(7-36)NH$_2$ or 10 nM human Gcg.

A relative $EC_{50}$ value and percent top ($E_{max}$) are derived by non-linear regression analysis using the percent maximal response vs. the concentration of peptide added, fitted to a four-parameter logistic equation (Genedata Screener®).

Functional data for Compounds 1-4, human GLP-1(7-36)NH$_2$, human Gcg and wild type human OXM are shown in Table 5 below. Means for $EC_{50}$ are expressed as Geometric means±standard error of the mean (SEM) with the number of replicates (n) indicated in parenthesis. Means for $E_{max}$ are expressed as the arithmetic mean±standard error. ND signifies that agonist activity was not detected. All values shown are to three (3) significant digits.

SH30027) supplemented with 10% fetal bovine serum, 10 mM HEPES, 1 mM sodium pyruvate, 2 mM L-Glutamine, 50 μM 2-Mercaptoethanol, and 100 U/ml Penicillin/100 μg/ml Streptomycin in a 37° C., 5% CO$_2$ incubator and passed twice weekly.

Performance of the assay requires detachment of the cells from culture flasks using Enzyme Free Cell Stripper and pelleted by centrifugation at 1000 rpm for 5 minutes at room temperature. The cell pellet is resuspended in the Earle's Balanced Salt Solution (EBSS) supplemented with 11.2 mM glucose & 0.1% BSA. 40 μl of cell suspension at density 1×10$^6$/ml are placed in 96-well half-area black plates (Costar 3875) and incubated in 37° C., 5% CO$_2$ incubator for 2 hours for recovery & starvation. Serial dilutions of test compounds are prepared at 100× final testing concentration in 100% DMSO, and further diluted 20 fold in EBSS supplemented with 11.2 mM glucose, 0.1% BSA, and 1.25 mM IBMX (Sigma I-7816). After 2 hours starvation, cells are treated with compound by adding 10 μl of 5× compound dilutions into the cell plates (n=2) and incubated in a 37° C., 5% CO$_2$ incubator for 30 minutes.

cAMP concentration is measured using a HTRF cAMP assay kit (Cisbio): cAMP-d2 conjugate in cell lysis buffer (20 μl) followed by the antibody anti-cAMP-Eu$^{3+}$-Cryptate, also in cell lysis buffer (20 μl), is added to the cells of the plate. The resulting competitive assay is incubated for at least 60 minutes at room temperature and is subsequently detected using a PerkinElmer Envision® instrument with excitation at 320 nm and emission at 665 nm and 620 nm. Envision units (emission at 665 nm/620 nm*10,000) are inversely proportional to the amount of cAMP present and are converted to nM cAMP per well using a cAMP standard curve.

The concentration of cAMP in each well (nM) was calculated using a cAMP standard curve and converted to a percent of the maximal response observed with native GLP-1 peptide at 300 nM for curve fitting.

A relative $EC_{50}$ value and percent top (% $E_{max}$) are derived by non-linear regression analysis using the percent maximal response vs. the concentration of peptide added, fitted to a four-parameter logistic equation (GraphPad Prism

TABLE 5

Functional Potency ($EC_{50}$) and Efficacy ($E_{max}$) for Compounds 1-4 human GLP-1(7-36)NH$_2$, human Gcg and wild type human OXM

| | Human GLP-1-R | | Human Gcg-R | |
|---|---|---|---|---|
| Compound | $EC_{50}$, nM ± SEM (n) | $E_{max}$,% | $EC_{50}$, nM ± SEM, (n) | $E_{max}$, % |
| Compound 1 | 23.9 ± 4.5 (13) | 104 ± 7 | 7.21 ± 1.06 (13) | 112 ± 3 |
| Compound 2 | 83.1 ± 16.8 (15) | 107 ± 7 | 26.5 ± 2.2 (15) | 114 ± 5 |
| Compound 3 | 34.3 ± 9.4 (13) | 105 ± 5 | 15.3 ± 2.2 (13) | 104 ± 5 |
| Compound 4 | 106 ± 18 (13) | 85.2 ± 6.0 | 68.8 ± 7.2 (15) | 116 ± 4 |
| Human Gcg | ND | ND | 0.023 ± 0.014 (47) | 113 ± 1 |
| Human GLP-1(7-36) NH$_2$ | 0.168 ± 0.008 (51) | 101 ± 1 | ND | ND |
| Wild type human OXM | 9.54 ± 1.34 (8) | 96.9 ± 5.7 | 0.757 ± 0.090 (8) | 121 ± 7 |

Functional Activation of the Rat GLP-1-R in Insulinoma Cell Line INS1 832-3

A rat pancreatic beta cell line, INS1 832-3 cell, is used to determine functional activity of Compounds 1-4 on stimulating cAMP production at the endogenous GLP-1 receptors. Cells are maintained in RPMI 1640 medium (HyClone, Cat#

(Version 6.05) software). The assay is performed with duplicated plates. The number of replicates (n) is indicated in parenthesis.

$EC_{50}$ and % $E_{max}$ for wild type human OXM, semaglutide and Compounds 1 and 2 were calculated essentially as described above. The $EC_{50}$ and % $E_{max}$ data for these compounds are provided in Table 6. Furthermore, Compounds 1 and 2 increased cAMP production in a dose-dependent manner (data not shown).

TABLE 6

$EC_{50}$ of wild type human OXM, semaglutide and Compounds 1 and 2 at the rat GLP-1-R in insulinoma cell line INS1 832-3

| Compound | $EC_{50}$ (nM) | $E_{max}$ (%) |
|---|---|---|
| Wild type human OXM | 7.3 (n = 1) | 121.1 |
| Semaglutide | 5.8 (n = 1) | 107.2 |
| Compound 1 | 26.1 (n = 1) | 112.3 |
| Compound 2 | 62 (n = 1) | 104.5 |

Functional Activation of hGcg-R in Primary Human Hepatocytes

Primary human hepatocytes are used to determine functional activity of compounds on stimulating cAMP production at the endogenous Gcg receptors. Vials of human primary hepatocytes are frozen in a liquid nitrogen tank. Upon removal, vials are thawed immediately in a water bath having a temperature of 37° C. Cell suspension is then transferred to 50 ml CHRM (Gibco/Life Technologies cat#CM7000 Cryopreserved Hepatocyte Recovery Medium).

The cell suspension is centrifuged at 1,000×g for 10 min. Cell pellets are resuspended in 5 ml of Plating Media after removing the CHRM by aspiration. The Plating Media is prepared by adding entire contents of CM3000 Supplement Packs to 500 ml Williams Media (Gibco/Life Technologies), followed by sterile filtration through a 0.22 μm membrane.

The cell density is counted on hemocytometer, by adding 100 μl of cell suspension to 100 μl Trypan Blue (HyClone Trypan Blue 0.04%, catalog number SV30084.01). The cell suspension is further diluted in the Plating Media to the final cell density of 0.8×10⁶ cells per ml. 65 ml of Plating Media is added to each well of the Collagen coated 96-well plate (Corning BioCoat, catalog number 354649, Lot#22314033). 65 ml of the cell suspension is then added to each well of the Collagen coated 96-well plate to final cell density 50,000 cells per well. The cell plate is incubated in a 37° C., 5% $CO_2$ incubator for 3-4 hours.

After 3-4 hours incubation, the media is aspirated and replaced with 100 ml Maintenance Media. The maintenance media is prepared by adding entire contents of CM4000 Supplement Packs to 500 ml Williams Media (Gibco/Life Technologies), followed by sterile filtration through a 0.22 μm membrane. The cell plate is returned to the 37° C., 5% $CO_2$ incubator overnight in preparation for the cAMP assay.

In preparation for the assay, compounds 1 and 2 and wild type human OXM are subjected to 3-fold serial dilution in the Compound Assay Buffer (HBSS containing 20 mM HEPES and 1% Heat-Inactivated FBS) for 10 concentrations.

The cell plate is removed from the incubator and the media is removed by gentle aspiration without disturbing the cell monolayer. The cells are treated by adding 40 μl of the Cell Assay Buffer and 40 μl of test solution (i.e. Compound 1, Compound 2 or wild-type human OXM diluted in Compound Assay Buffer) into the cell plates and incubating at room temperature for 1 hour with gentle agitation.

cAMP concentration is measured using a HTRF cAMP assay kit (Cisbio): cAMP-d2 conjugate in cell lysis buffer (40 μl) followed by the antibody anti-cAMP-$Eu^{3+}$-Cryptate, also in cell lysis buffer (40 μl), is added to the cells of the plate. The resulting competitive assay is incubated for at least 60 minutes at room temperature, then detected using a PerkinElmer Envision® instrument with excitation at 320 nm and emission at 665 nm and 620 nm. Envision units (emission at 665 nm/620 nm*10,000) are inversely proportional to the amount of cAMP present and are converted to nM cAMP per well using a cAMP standard curve.

The concentration of cAMP in each well (nM) is calculated using a cAMP standard curve and converted to a percent of the maximal response observed with a Gcg analog conjugated to a saturated C18 fatty acid (diacid) for curve fitting.

A relative $EC_{50}$ value and percent top (% $E_{max}$) are derived by non-linear regression analysis using the percent maximal response vs. the concentration of peptide added, fitted to a four-parameter logistic equation (GraphPad Prism (Version 6.05) software).

$EC_{50}$ and % $E_{max}$ for Compounds 1 and 2 and wild type human OXM were calculated essentially as described above. The $EC_{50}$ and % $E_{max}$ data for these compounds is provided in Table 7. Furthermore, Compounds 1 and 2 increased cAMP production in a dose-dependent manner (data not shown). The number of replicates (n) is indicated in parenthesis.

TABLE 7

$EC_{50}$ of Compounds 1 and 2 and wild type human OXM at the hGcg-R in Primary Human Hepatocytes

| Compound | $EC_{50}$ (nM) | $E_{max}$ (%) |
|---|---|---|
| Wild type human OXM | 29.8 (n = 1) | 90.0 |
| Compound 1 | 99.9 (n = 1) | 100.0 |
| Compound 2 | 159.4 (n = 1) | 101.2 |

Pharmacokinetics

Pharmacokinetics in Cynomolgus Monkeys

The in vivo pharmacokinetic properties for compounds of the present invention are demonstrated using cynomolgus monkeys.

The compounds are administered by a single intravenous or subcutaneous dose of 50 nmole/kg or 250 nmole/kg. Blood is collected from each animal at 4, 8, 12, 24, 48, 72, 96, 120, 144, 168, 192, 240, 288, 208, 480, 576 and 672 hours post-dosage.

The plasma concentrations of compounds are determined by a LC/MS method. Briefly, a compound of the present invention is extracted from 100% monkey plasma (25 μl) using acetonitrile. Two distinct layers are formed upon centrifugation with the compound located in the liquid layer. An 80 μl aliquot of the supernatant was transferred to a 96-well plate, diluted with 150 μl of water and 25 μl of formic acid. The diluted sample (10 μl) was injected onto a Supelco Analytical Discovery BIO Wide Pore C5-3, 5 cm×1 mm, 3 um column. The column effluent is directed into a Thermo Q-Exactive mass spectrometer for detection and quantitation.

In experiments performed essentially as described for this assay, cynomolgus monkeys were administered a single subcutaneous (50 nmole/kg) dose of Compound 1 in 40 mM Tris HCl (pH 8.0) at a volume of 0.20 mL/kg. Blood was collected from each animal at 2 (IV only), 7, 12, 24, 48, 72, 96, 120, 168, 192, 240, 336, 480, 576, and 672 hours post dose.

Other cynomolgus monkeys were administered a single intravenous (50 nmole/kg) or subcutaneous (50 or 250 nmole/kg) dose of Compound 2 in 40 mM Tris HCl (pH 8.0) at a volume of 0.20 mL/kg. Blood was collected from each animal at 2 (IV only), 7, 12, 24, 48, 72, 96, 120, 168, 192, 240, 336, 480, 576, and 672 hours post dose.

The data for Compound 1 is provided in Table 9 and the data for Compound 2 is provided in Table 10.

Compound 1 reached mean maximum plasma concentrations approximately 12 hours following the 50 nmol/kg subcutaneous dose. The mean half-life is 57 hours and the mean clearance is 2.16 mL/hour/kg (Table 8).

Compound 2 reached mean maximum plasma concentrations approximately 24 hours following the 50 nmol/kg subcutaneous dose. The mean half-life is 122 hours and the mean clearance is 0.55 mL/hour/kg (Table 9).

TABLE 8

Individual and mean pharmacokinetic parameters following a single 50 nmol/kg subcutaneous dose of Compound 1 to male cynomolgus monkeys

| Compound | Animal ID | $T_{1/2}$ (hour) | $T_{max}$ (hour) | $C_{max}$ (nmol/L) | $AUC_{0-inf}$ (hr * nmol/L) | CL/F (mL/hr/kg) |
|---|---|---|---|---|---|---|
| Compound 1: SC 50 nmol/kg | I07762 | 47 | 12 | 253 | 21672 | 2.31 |
| | I07763 | 67 | 12 | 236 | 24865 | 2.01 |
| | Mean | 57 | 12 | 244 | 23268 | 2.16 |

Abbreviations:
$AUC_{0-inf}$ = area under the curve from 0 to infinity,
CL/F = clearance/bioavailability,
$T_{max}$ = time to maximum concentration,
$C_{max}$ = maximum plasma concentration,
$T_{1/2}$ = half-life.

TABLE 9

Individual and mean pharmacokinetic parameters of Compound 2 following a single intravenous or subcutaneous dose to male cynomolgus monkeys

| Compound/Route/Dose | Animal ID | $T_{1/2}$ (hour) | $T_{max}$ (hour) | $C_0$ or $C_{max}$ (nmol/L) | $AUC_{0-inf}$ (hr * nmol/L) | CL/F (mL/hr/kg) |
|---|---|---|---|---|---|---|
| Compound 2: IV 50 nmol/kg | I07772 | 88 | NA | 1017 | 94828 | 0.53 |
| | I07773 | 131 | NA | 1105 | 93174 | 0.54 |
| | Mean | 110 | NA | 1061 | 94001 | 0.53 |
| Compound 2: SC 50 nmol/kg | I07764 | 137 | 24 | 474 | 100967 | 0.50 |
| | I07765 | 106 | 24 | 452 | 82792 | 0.60 |
| | Mean | 122 | 24 | 463 | 91879 | 0.55 |
| Compound 2: SC 250 nmol/kg | I07766 | 115 | 12 | 3640 | 429859 | 0.58 |
| | I07767 | 104 | 12 | 3615 | 540175 | 0.46 |
| | Mean | 110 | 12 | 3628 | 485017 | 0.52 |

Abbreviations:
$AUC_{0-inf}$ = area under the curve from 0 to infinity,
CL = clearance,
CL/F = clearance/bioavailability,
$T_{max}$ = time to maximal concentration,
$C_0$ = concentration extrapolated to time 0 hour,
$C_{max}$ = maximal plasma concentration,
$T_{1/2}$ = half-life,
NA = not applicable.

In Vivo Studies

Oral Glucose Tolerance Test (OGTT) in DIO Mice

Diet-induced obese (DIO) mouse model is a model of insulin resistance. Five to six months old male DIO mice (C57BL/6) from Taconic Biosciences are used in this study. Animals are individually housed in a temperature-controlled (24° C.) facility with a 12 hour light/dark cycle (lights on 06:00), and free access to food and water. The acclimation period to the facility is two weeks. The day before the study, animals are randomized into groups based on their body weight. That same afternoon, animals are fasted in clean cages and dosed with vehicle (40 mM Tris-HCl, pH 8.0) or test articles by subcutaneous injection. The following morning, 16 hours post the peptide injection, fasting body weights are obtained to calculate glucose doses. Blood samples are taken to measure time zero glucose. Animals are then given an oral gavage of glucose (2 g/kg). Two glucose readings via glucometers were obtained at 15, 30, 60 and 120 minutes post oral glucose. The average of two glucose readings is reported at each time point and an area under the curve is calculated. Statistics were analyzed using ANOVA with Dunnett's comparison by JMP 6; significance is denoted at $p \leq 0.05$ vs. vehicle.

In experiments performed essentially as described in this assay, Compound 2 showed a dose-dependent decrease in glucose during the tolerance test, and the glucose AUC was decreased at all three doses tested 1, 3 and 10 nmol/kg (Table 10).

TABLE 10

Glucose AUC of male DIO mice treated with Compound 2 and semaglutide in response to an OGTT (2 g/kg)

| Compound | Dose (nmol/kg) | Glucose AUC (% of vehicle) |
|---|---|---|
| Compound 2 | 1 | 76* |
| Compound 2 | 3 | 50* |
| Compound 2 | 10 | 39* |
| Semaglutide | 1 | 59* |
| Semaglutide | 3 | 51* |
| Semaglutide | 10 | 38* |

% of vehicle calculated as 100 × (Value calculated for compound group/value calculated for vehicle group)
*$p \leq 0.05$ OGTT in Streptozotocin (STZ)-Treated DIO Mice STZ-treated mouse model is a model of early diabetes. Five to six months old male DIO mice (C57BL/6) from Taconic Biosciences are used in this study. Animals are individually housed in a temperature-controlled (24° C.) facility with a 12 hour light/dark cycle (lights on 6:00), and free access to food and water. After two weeks acclimation to the facility, mice are injected intraperitoneally with 50 mg/kg of STZ on Tuesday and Friday. Two weeks post the injection, animals with glucose levels between 180-300 mg/dL at 09:00 are selected for the OGTT study. The day before the study, animals are randomized into groups based on body weight and their glucose levels. Animals are treated with vehicle or testing articles by subcutaneous injection just prior to food removal overnight (16:00). The following morning at 08:00, 16 hours post compound injection, blood samples are taken to measure time zero glucose. Animals are given an oral dose of glucose of 2 g/kg. Glucose is measured 15, 30, 60, and 120 minutes post the oral glucose challenge. Statistics are analyzed using ANOVA with Dunnett's comparison by JMP 6. Significance is denoted at $p \leq 0.05$ vs. vehicle.

In experiments performed essentially as described in this assay, Compound 2 showed a dose dependent decrease in glucose excursion during the tolerance test. The glucose AUC was decreased at all three doses tested 1, 3 and 10 nmol/kg (Table 11).

TABLE 11

Glucose AUC of male STZ mice treated with Compound 2 and semaglutide in response to an OGTT (2 g/kg)

| Compound | Dose (nmol/kg) | Glucose AUC (% of vehicle) |
|---|---|---|
| Compound 2 | 1 | 70* |
| Compound 2 | 3 | 48* |
| Compound 2 | 10 | 35* |
| Semaglutide | 1 | 72* |

TABLE 11-continued

Glucose AUC of male STZ mice treated with Compound 2 and semaglutide in response to an OGTT (2 g/kg)

| Compound | Dose (nmol/kg) | Glucose AUC (% of vehicle) |
|---|---|---|
| Semaglutide | 3 | 53* |
| Semaglutide | 10 | 35* |

% of vehicle calculated as 100 × (Value calculated for compound group/value calculated for vehicle group)
*$p \leq 0.05$ Glycemic Control in DIO Mice Five to six months old male DIO mice (C57BL/6) from Taconic Biosciences are used in this study. Animals are individually housed in a temperature-controlled (24° C.) facility with a 12 hour light/dark cycle (lights on 6:00), and free access to food and water. After two weeks acclimation to the facility, the mice are randomized to treatment groups (n=7/group) based on their body weight and blood glucose. Mice are injected subcutaneously once with vehicle or compounds (25 nmol/kg). Blood glucose is monitored 2 and 8 hours post-injection and then once a day at 08:00 for 4 days. OGTTs are performed at 44 and 78 hours post the peptide injection. Statistics are analyzed using ANOVA with Dunnett's comparison by JMP 6. Significance is denoted at $p \leq 0.05$ vs vehicle.

In experiments performed essentially as described in this assay, Compound 2 and Compound 4 treated mice had lower glucose than the vehicle controls up to 96 hours post injection. Compound 2 and Compound 4 treated mice had lower glucose excursions post an oral glucose challenge at both time points when the OGTT was performed.

Compound 1 and Compound 3 decreased blood glucose for up to 72 hours (Table 12). Compound 1 and Compound 3 treated mice had lower glucose excursions post an oral glucose challenge at 44 hour post the peptide injection (Table 13).

TABLE 12

Blood glucose measured at 2, 8, 24, 48, 72 and 96 hours post-injection in male DIO mice

| | Blood glucose (mg/dL) post-injection of Vehicle | | Blood glucose (mg/dL) post-injection of Compound 1 | | Blood glucose (mg/dL) post-injection of Compound 2 | | Blood glucose (mg/dL) post-injection of Compound 3 | | Blood glucose (mg/dL) post-injection of Compound 4 | |
|---|---|---|---|---|---|---|---|---|---|---|
| Time | Mean | SEM | Mean | SEM | Mean | SEM | Mean | SEM | Mean | SEM |
| 2 | 155.7 | 5.0 | 168.5 | 21.4 | 112.7 | 8.5 | 173.4 | 19.0 | 110.2 | 2.3 |
| 8 | 164.5 | 6.7 | 79.4 | 3.4 | 87.4 | 1.2 | 81.4 | 3.8 | 91.5 | 4.4 |
| 24 | 189.1 | 5.1 | 90.6 | 4.0 | 101.1 | 3.1 | 96.6 | 2.8 | 87.4 | 1.6 |
| 48 | 142.6 | 2.5 | 101.9 | 4.1 | 101.3 | 3.1 | 95.8 | 5.3 | 102.9 | 4.7 |
| 72 | 154.2 | 4.2 | 113.4 | 5.6 | 97.6 | 3.8 | 104.7 | 5.6 | 115.7 | 2.8 |
| 96 | 159.4 | 4.3 | 150.0 | 10.4 | 115.0 | 5.5 | 141.1 | 7.2 | 104.6 | 2.6 |

TABLE 13

Glucose excursions during OGTTs at 44 hours and 78 hours post-injection of compound

| Compound | 44 hours Glucose AUC (% of Vehicle) | 78 hours Glucose AUC (% of Vehicle) |
|---|---|---|
| Compound 1 | 42* | 90 |
| Compound 2 | 39* | 66* |
| Compound 3 | 35* | 76* |
| Compound 4 | 41* | 60* |

% of vehicle calculated as 100 × (Value calculated for compound group/value calculated for vehicle group)
*$p \leq 0.05$ Chronic Treatment in DIO Mice The effects on food intake and body weight/fat are evaluated in DIO mice. Five to six months old DIO mice (C57BL/6) from Taconic Biosciences are used in this study. Animals are individually housed in a temperature-controlled (24° C.) facility with a 12 hour light/dark cycle (lights on 6:00), and free access to food and water. The mice are acclimated to the facility for two weeks. The day before the study start, fat mass is measured by nuclear magnetic resonance (NMR) using an Echo Medical System (Houston, Tex.) instrument. The mice are randomized to treatment groups (N=7/group) based on body weight and fat mass so each group had similar starting mean body weight and fat mass. Vehicle (40 mM Tris-HCl, pH 8.0), test compounds, or a positive control semaglutide are administered by subcutaneous (SC) injection to ad libitum mice between 8-10 am every three days for 15 days. SC injections are made on Day 1, 4, 7, 10, and 13. Body weight and food intake are measured right before each injection throughout the study. Percent changes in body weight are calculated as follows:

$$\frac{100 \times (\text{Final body weight of animal} - \text{Initial body weight of animal})}{\text{Initial body weight of animal}}$$

At the completion of the study, total fat mass is measured again by NMR. Statistics are analyzed using ANOVA with Dunnett's comparison by JMP 6. Significance is denoted at $p \leq 0.05$ vs. vehicle.

In experiments performed essentially as described in this assay, Compounds 1-4 reduce food intake and body weight/fat as shown in Table 14 below:

TABLE 14

% Body Weight change and % Body Fat change in DIO mice

| Compound | Dose (nmol/kg) | Body Weight (% change vs. vehicle from Day 1) | Body Fat (% change vs. vehicle from Day 1) |
| --- | --- | --- | --- |
| Compound 1 | 15 | −19* | −49* |
|  | 30 | −29* | −66* |
| Compound 2 | 15 | −19* | −43* |
|  | 30 | −33* | −70* |
| Compound 3 | 15 | −17* | −32* |
|  | 30 | −37* | −67* |
| Compound 4 | 15 | −15* | −26* |
|  | 30 | −39* | −69* |
| Semaglutide | 30 | −8 | −20* |
|  | 60 | −12* | −29* |

*p ≤ 0.05

Acute Treatment in DIO Mice

In order to investigate metabolic pathways involved with the treatment of compounds of the present invention independent of weight loss, compounds are tested in DIO mice (C57BL/6) acutely. The mice used are three to four months old on a high fat diet for at least 4 weeks. Animals are individually housed in a temperature-controlled (24° C.) facility with a 12 hour light/dark cycle (lights on 6:00), and free access to food and water. Vehicle or testing compounds were administered to mice by subcutaneous injection at 16:00 the day before the study day. Animals were sacrificed 16 hours later to collect blood via cardia puncture. Statistics are analyzed using ANOVA with Dunnett's comparison for JMP-6. Significance is denoted at p≤0.05 vs vehicle.

In experiments performed essentially as described in the assay, Compounds 1-3 decrease serum cholesterol and PCSK9 levels and increase FGF-21 levels as shown in Table 15. In contrast, treatment with semaglutide does not decrease serum cholesterol and PCSK9 levels and increase FGF-21 levels. Food intake was decreased to a similar level in all treatment groups, which may indicate that changes in cholesterol, PCSK9 and FGF-21 are food-intake independent.

TABLE 15

Acute effects on PCSK9, FGF-21 and Cholesterol levels

| Compound | Dose (nmol/kg) | PCSK9 (% of vehicle) | FGF-21 (% of vehicle) | Cholesterol (% of vehicle) |
| --- | --- | --- | --- | --- |
| Compound 1 | 30 | 14.6* | 1770* | 60.9* |
| Compound 2 | 30 | 12.8* | 465* | 80.6* |
| Compound 3 | 30 | 15.6* | 1124* | 55.6* |
| Semaglutide | 30 | 115.3 | 75 | 117.6 |

% of vehicle calculated as 100 × (Value calculated for compound group/value calculated for vehicle group)
*p ≤ 0.05

Effects on Energy Expenditure in DIO Mice

Seven to eight months old male DIO mice (C57BL/6) weighing 45-50 g are used in this study to assess the effect of compounds of the present invention on energy metabolism. Animals are individually housed in a temperature-controlled (24° C.) facility with a 12 hour light/dark cycle (lights on 22:00), and free access to food (TD95217)(Teklad) and water. After 2 weeks acclimation to the facility, mice are randomized to treatment groups (N=6/group) based on body weight so each group has similar starting mean body weight. Animals are placed in a PhenoMaster/LabMaster calorimeter (TSE Systems, Chesterfield, Mo.) for 8 days of acclimation. Vehicle (40 mM Tris HCl buffer at pH 8.0, 10 ml/kg), test article (15 nmol/kg) or semaglutide (60 nmol/kg) are subcutaneously administered to ad libitum fed DIO mice 30-90 minutes prior to the onset of the dark cycle every three days for 15 days.

Heat and respiratory quotient (RER) are measured by indirect calorimetry as described using an open-circuit calorimetry system. RER is the ratio of the volume of $CO_2$ produced ($VCO_2$) to the volume of $O_2$ consumed ($VO_2$). Heat is calculated with lean body weight considered. The energy expenditure is kcal/kg/3 day and expressed as mean±SEM of 6 mice per group. Statistical significance is assessed by two-way ANOVA followed by Tukey's multiple comparison test.

In experiments performed essentially as described in this assay, mice treated with Compounds 1 and 2 increased their metabolic rate starting from Week 2 and sustained the effect throughout the treatment period as shown in Table 16. However, semaglutide had no effect on metabolic rate. This increase in metabolic rate may contribute to additional weight loss observed with administration of Compounds 1 and 2 in comparison with administration of semaglutide.

TABLE 16

Effect of chronic treatment with Compound 1, Compound 2 or semaglutide on metabolic rate in DIO mice

| | Cumulative Heat (Kcal/kg lean mass/3 day) | | | |
| --- | --- | --- | --- | --- |
| Treatment Period | Vehicle | Semaglutide | Compound 1 | Compound 2 |
| Day 1 to Day 4 | 2184 ± 27 | 1973 ± 51 | 1749 ± 136** | 1746 ± 96** |
| Day 4 to Day 7 | 2154 ± 36 | 2018 ± 54 | 1822 ± 173 | 1778 ± 132* |
| Day 7 to Day 10 | 2239 ± 28 | 2151 ± 48 | 2349 ± 129 | 2549 ± 129** |
| Day 10 to Day 13 | 2207 ± 16 | 2138 ± 46 | 2351 ± 144 | 2568 ± 147* |

*p ≤ 0.05 vs. vehicle
**p ≤ 0.05 vs. semaglutide

Amino Acid Sequences (Human OXM)
SEQ ID NO: 1
His-Ser-Gln-Gly-Thr-Phe-Thr-Ser-Asp-Tyr-Ser-Lys- Tyr-Leu-Asp-Ser-Arg-Arg-Ala-Gln-Asp-Phe-Val-Gln- Trp-Leu-Met-Asn-Thr-Lys-Arg-Asn-Arg-Asn-Asn-Ile- Ala (HSQGTFTSDYSKYLDSRRAQDFVQWLMNTKRNRNNIA)

(Artificial Sequence)
SEQ ID NO: 2
His-Xaa2-Gln-Gly-Thr-Phe-Thr-Ser-Asp-Tyr-Ser-Lys- Tyr-Leu-Asp-Glu-Lys-Lys-Ala-Lys-Glu-Phe-Val-Glu- Trp-Leu-Leu-Xaa28-Gly-Gly-Pro-Ser-Ser-Gly (HXaa2QGTFTSDYSKYLDEKKAKEFVEWLLXaa28GGPSSG)

wherein Xaa2 is Aib;
Xaa28 is Glu (E) or Ser (S);
Lys at position 20 is chemically modified by conjugation of the epsilon-amino group of the Lys side chain with a C14-C24 fatty acid via (i) a direct bond or (ii) a linker between the Lys at position 20 and the C14-C24 fatty acid; and the C-terminal amino acid is optionally amidated.

(Artificial Sequence)

SEQ ID NO: 3

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Glu-Gly-Gly-Pro-Ser-Ser-Gly (HXaa2QGTFTSDYSKYLDEKKAKEFVEWLLEGGPSSG)

wherein Xaa2 is Aib;
Lys at position 20 is chemically modified by conjugation of the epsilon-amino group of the Lys side chain with a C14-C24 fatty acid via (i) a direct bond or (ii) a linker between the Lys at position 20 and the C14-C24 fatty acid; and
the C-terminal amino acid is optionally amidated.

(Artificial Sequence)

SEQ ID NO: 4

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Ser-Gly-Gly-Pro-Ser-Ser-Gly (HXaa2QGTFTSDYSKYLDEKKAKEFVEWLLSGGPSSG)

wherein Xaa2 is Aib;
Lys at position 20 is chemically modified by conjugation of the epsilon-amino group of the Lys side chain with a C14-C24 fatty acid via (i) a direct bond or (ii) a linker between the Lys at position 20 and the C14-C24 fatty acid; and
the C-terminal amino acid is optionally amidated.

(Artificial Sequence)

SEQ ID NO: 5

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Glu-Gly-Gly-Pro-Ser-Ser-Gly (HXaa2QGTFTSDYSKYLDEKKAKEFVEWLLEGGPSSG)

wherein Xaa2 is Aib;
Lys at position 20 is chemically modified by conjugation of the epsilon-amino group of the Lys side chain with ([2-(2-aminoethoxy)-ethoxy]-acetyl)$_2$-(γ-Glu)-CO—(CH$_2$)$_{16}$CO$_2$H; and
the C-terminal amino acid is amidated.

(Artificial Sequence)

SEQ ID NO: 6

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Glu-Gly-Gly-Pro-Ser-Ser-Gly (HXaa2QGTFTSDYSKYLDEKKAKEFVEWLLEGGPSSG)

wherein Xaa2 is Aib;
Lys at position 20 is chemically modified by conjugation of the epsilon-amino group of the Lys side chain with ([2-(2-aminoethoxy)-ethoxy]-acetyl)$_2$-(γ-Glu)-CO—(CH$_2$)$_{18}$CO$_2$H; and
the C-terminal amino acid is amidated.

(Artificial Sequence)

SEQ ID NO: 7

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Ser-Gly-Gly-Pro-Ser-Ser-Gly (HXaa2QGTFTSDYSKYLDEKKAKEFVEWLLSGGPSSG)

wherein Xaa2 is Aib;
Lys at position 20 is chemically modified by conjugation of the epsilon-amino group of the Lys side chain with ([2-(2-aminoethoxy)-ethoxy]-acetyl)$_2$-(γ-Glu)$_2$-CO—(CH$_2$)$_{16}$CO$_2$H; and
the C-terminal amino acid is amidated.

(Artificial Sequence)

SEQ ID NO: 8

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Ser-Gly-Gly-Pro-Ser-Ser-Gly (HXaa2QGTFTSDYSKYLDEKKAKEFVEWLLSGGPSSG)

wherein Xaa2 is Aib;
Lys at position 20 is chemically modified by conjugation of the epsilon-amino group of the Lys side chain with ([2-(2-aminoethoxy)-ethoxy]-acetyl)$_2$-(γ-Glu)$_2$-CO—(CH$_2$)$_{18}$CO$_2$H; and
the C-terminal amino acid is amidated.

(Artificial Sequence)

SEQ ID NO: 9

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Xaa28-Gly-Gly-Pro-Ser-Ser-Gly (HXaa2QGTFTSDYSKYLDEKKAKEFVEWLLXaa28GGPSSG)

wherein Xaa2 is Aib;
Xaa28 is Glu (E) or Ser (S); and
the C-terminal amino acid is optionally amidated.

(Artificial Sequence)

SEQ ID NO: 10

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Glu-Gly-Gly-Pro-Ser-Ser-Gly (HXaa2QGTFTSDYSKYLDEKKAKEFVEWLLEGGPSSG)

wherein Xaa2 is Aib; and
the C-terminal amino acid is optionally amidated.

(Artificial Sequence)

SEQ ID NO: 11

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Ser-Gly-Gly-Pro-Ser-Ser-Gly (HXaa2QGTFTSDYSKYLDEKKAKEFVEWLLSGGPSSG)

wherein Xaa2 is Aib; and
the C-terminal amino acid is optionally amidated.

SEQUENCE LISTING

<160> NUMBER OF SEQ ID NOS: 11

<210> SEQ ID NO 1
<211> LENGTH: 37
<212> TYPE: PRT
<213> ORGANISM: Homo sapien

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 2
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Lys at position 20 is chemically modified by
      conjugation of the epsilon-amino group of the Lys side chain with
      a C14-C24 fatty acid via (i) a direct bond or (ii) a linker
      between the Lys at position 20 and the C14-C24 fatty acid
<220> FEATURE:
<221> NAME/KEY: MISC_FEATURE
<222> LOCATION: (28)..(28)
<223> OTHER INFORMATION: Xaa at position 28 is Glu or Ser
<220> FEATURE:
<221> NAME/KEY: MOD_RES
<222> LOCATION: (34)..(34)
<223> OTHER INFORMATION: Gly at position 34 is optionally amidated

<400> SEQUENCE: 2

His Xaa Gln Gly Thr Phe Thr Ser Asp Tyr Ser Lys Tyr Leu Asp Glu
1               5                   10                  15

Lys Lys Ala Lys Glu Phe Val Glu Trp Leu Leu Xaa Gly Gly Pro Ser
            20                  25                  30

Ser Gly

<210> SEQ ID NO 3
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib

```
<220> FEATURE:
<221> NAME/KEY: MOD_RES
<222> LOCATION: (20)..(20)
<223> OTHER INFORMATION: Lys at position 20 is chemically modified by
      conjugation of the epsilon-amino group of the Lys side chain with
      a C14-C24 fatty acid via (i) a direct bond or (ii) a linker
      between the Lys at position 20 and the C14-C24 fatty acid
<220> FEATURE:
<221> NAME/KEY: MOD_RES
<222> LOCATION: (34)..(34)
<223> OTHER INFORMATION: Gly at position 34 is optionally amidated

<400> SEQUENCE: 3

His Xaa Gln Gly Thr Phe Thr Ser Asp Tyr Ser Lys Tyr Leu Asp Glu
1               5                   10                  15

Lys Lys Ala Lys Glu Phe Val Glu Trp Leu Leu Glu Gly Gly Pro Ser
            20                  25                  30

Ser Gly

<210> SEQ ID NO 4
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Lys at position 20 is chemically modified by
      conjugation of the epsilon-amino group of the Lys side chain
      with a C14-C24 fatty acid via (i) a direct bond or (ii) a linker
      between the Lys at position 20 and the C14-C24 fatty acid
<220> FEATURE:
<221> NAME/KEY: MOD_RES
<222> LOCATION: (34)..(34)
<223> OTHER INFORMATION: Gly at position 34 is optionally amidated

<400> SEQUENCE: 4

His Xaa Gln Gly Thr Phe Thr Ser Asp Tyr Ser Lys Tyr Leu Asp Glu
1               5                   10                  15

Lys Lys Ala Lys Glu Phe Val Glu Trp Leu Leu Ser Gly Gly Pro Ser
            20                  25                  30

Ser Gly

<210> SEQ ID NO 5
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib
```

```
<220> FEATURE:
<221> NAME/KEY: MOD_RES
<222> LOCATION: (20)..(20)
<223> OTHER INFORMATION: Lys at position 20 is chemically modified by
      conjugation of the epsilon-amino group of the Lys side chain with
      ([2-(2-aminoethoxy)-ethoxy]-acetyl)2-(y-Glu)-CO-(CH2)16CO2H
<220> FEATURE:
<221> NAME/KEY: MOD_RES
<222> LOCATION: (34)..(34)
<223> OTHER INFORMATION: Gly at position 34 is amidated

<400> SEQUENCE: 5

His Xaa Gln Gly Thr Phe Thr Ser Asp Tyr Ser Lys Tyr Leu Asp Glu
1               5                   10                  15

Lys Lys Ala Lys Glu Phe Val Glu Trp Leu Leu Glu Gly Gly Pro Ser
            20                  25                  30

Ser Gly

<210> SEQ ID NO 6
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is a nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Lys at position 20 is chemically modified by
      conjugation of the epsilon-amino group of the Lys side chain with
      ([2-(2-aminoethoxy)-ethoxy]-acetyl)2-(y-Glu)-CO-(CH2)18CO2H
<220> FEATURE:
<221> NAME/KEY: MOD_RES
<222> LOCATION: (34)..(34)
<223> OTHER INFORMATION: Gly at position 34 is amidated

<400> SEQUENCE: 6

His Xaa Gln Gly Thr Phe Thr Ser Asp Tyr Ser Lys Tyr Leu Asp Glu
1               5                   10                  15

Lys Lys Ala Lys Glu Phe Val Glu Trp Leu Leu Glu Gly Gly Pro Ser
            20                  25                  30

Ser Gly

<210> SEQ ID NO 7
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MOD_RES
<222> LOCATION: (2)..(2)
<223> OTHER INFORMATION: Aib
```

```
<220> FEATURE:
<221> NAME/KEY: MOD_RES
<222> LOCATION: (20)..(20)
<223> OTHER INFORMATION: Lys at position 20 is chemically modified by
      conjugation of the epsilon-amino group of the Lys side chain with
      ([2-(2-aminoethoxy)-ethoxy]-acetyl)2-(y-Glu)2-CO-(CH2)16CO2H
<220> FEATURE:
<221> NAME/KEY: MOD_RES
<222> LOCATION: (34)..(34)
<223> OTHER INFORMATION: Gly at position 34 is amidated

<400> SEQUENCE: 7

His Xaa Gln Gly Thr Phe Thr Ser Asp Tyr Ser Lys Tyr Leu Asp Glu
1               5                   10                  15

Lys Lys Ala Lys Glu Phe Val Glu Trp Leu Leu Ser Gly Gly Pro Ser
            20                  25                  30

Ser Gly

<210> SEQ ID NO 8
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Lys at position 20 is chemically modified by
      conjugation of the epsilon-amino group of the Lys side chain with
      ([2-(2-aminoethoxy)-ethoxy]-acetyl)2-(y-Glu)2-CO-(CH2)18CO2H
<220> FEATURE:
<221> NAME/KEY: MOD_RES
<222> LOCATION: (34)..(34)
<223> OTHER INFORMATION: Gly at position 34 is amidated

<400> SEQUENCE: 8

His Xaa Gln Gly Thr Phe Thr Ser Asp Tyr Ser Lys Tyr Leu Asp Glu
1               5                   10                  15

Lys Lys Ala Lys Glu Phe Val Glu Trp Leu Leu Ser Gly Gly Pro Ser
            20                  25                  30

Ser Gly

<210> SEQ ID NO 9
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (28)..(28)
<223> OTHER INFORMATION: Xaa at position 28 is Glu or Ser
```

```
<220> FEATURE:
<221> NAME/KEY: MOD_RES
<222> LOCATION: (34)..(34)
<223> OTHER INFORMATION: Gly at position 34 is optionally amidated

<400> SEQUENCE: 9

His Xaa Gln Gly Thr Phe Thr Ser Asp Tyr Ser Lys Tyr Leu Asp Glu
1               5                   10                  15

Lys Lys Ala Lys Glu Phe Val Glu Trp Leu Leu Xaa Gly Gly Pro Ser
            20                  25                  30

Ser Gly

<210> SEQ ID NO 10
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (34)..(34)
<223> OTHER INFORMATION: Gly at position 34 is optionally amidated

<400> SEQUENCE: 10

His Xaa Gln Gly Thr Phe Thr Ser Asp Tyr Ser Lys Tyr Leu Asp Glu
1               5                   10                  15

Lys Lys Ala Lys Glu Phe Val Glu Trp Leu Leu Glu Gly Gly Pro Ser
            20                  25                  30

Ser Gly

<210> SEQ ID NO 11
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-aminoisobutyric Acid
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (34)..(34)
<223> OTHER INFORMATION: Gly at position 34 is optionally amidated

<400> SEQUENCE: 11

His Xaa Gln Gly Thr Phe Thr Ser Asp Tyr Ser Lys Tyr Leu Asp Glu
1               5                   10                  15

Lys Lys Ala Lys Glu Phe Val Glu Trp Leu Leu Ser Gly Gly Pro Ser
            20                  25                  30

Ser Gly
```

We claim:
1. A compound of the following formula:

```
His-Xaa2-Gln-Gly-Thr-Phe-Thr-Ser-Asp-Tyr-Ser-Lys-
Tyr-Leu-Asp-Glu-Lys-Lys-Ala-Lys-Glu-Phe-Val-Glu-
Trp-Leu-Leu-Xaa28-Gly-Gly-Pro-Ser-Ser-Gly
``` wherein
Xaa2 is Aib;
Xaa28 is Glu or Ser;
Lys at position 20 is chemically modified by conjugation of the epsilon-amino group of the Lys side chain with a C14-C24 fatty acid via (i) a direct bond or (ii) a linker between the Lys at position 20 and the C14-C24 fatty acid; and
the C-terminal amino acid is optionally amidated (SEQ ID NO: 2);
or a pharmaceutically acceptable salt thereof.

2. The compound of claim 1, or a pharmaceutically acceptable salt thereof, wherein the Lys at position 20 is chemically modified by conjugation with a C14-C24 fatty acid via a linker between the Lys at position 20 and the C14-C24 fatty acid and wherein the linker is selected from the group consisting of:
(a) an amino polyethylene glycol carboxylate of Formula I:

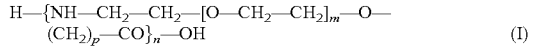

wherein m is any integer from 1 to 12, n is any integer from 1 to 12, and p is 1 or 2;
(b) an amino acid selected from the group consisting of arginine (Arg), asparagine (Asn), aspartic acid (Asp), glutamine (Gln), glutamic acid (Glu), histidine (His), lysine (Lys), serine (Ser), threonine (Thr), citrulline (Cit), ornithine (Orn), sarcosine (Sar), glycine (Gly), γ-aminobutyric acid (γ-Abu) and γ-glutamic acid (γ-Glu);
(c) a dipeptide selected from the group consisting of Ala-Ala, β-Ala-β-Ala, Glu-Glu, Gly-Gly, Leu-Leu, Pro-Pro, Ser-Ser, Thr-Thr, γ-glutamic acid (γ-Glu)-γ-glutamic acid (γ-Glu), Glu-γ-glutamic acid (γ-Glu), γ-glutamic acid (γ-Glu)-Glu, γ-aminobutyric acid (γ-Abu)-γ-aminobutyric acid (γ-Abu), 6-amino-hexanoic acid-6-aminohexanoic acid, 5-aminovaleric acid-5-aminovaleric acid, 7-aminoheptanoic acid-7-aminoheptanoic acid and 8-aminooctanoic acid-8-aminooctanoic acid;
(d) a tripeptide selected from the group consisting of Ala-Ala-Ala, β-Ala-β-Ala-β-Ala, Glu-Glu-Glu, γ-Glu-γ-Glu-γ-Glu, Glu-γ-Glu-γ-Glu, γ-Glu-γ-Glu-Glu, γ-Glu-Glu-γ-Glu, Gly-Gly-Gly, Gly-Gly-Ser, Ser-Gly-Gly, Gly-Ser-Gly, Gly-Gly-Glu, Glu-Gly-Gly, Gly-Glu-Gly, Gly-Gly-γ-Glu, γ-Glu-Gly-Gly, Gly-γ-Glu-Gly, Leu-Leu-Leu, Pro-Pro-Pro and γ-Abu-γ-Abu-γ-Abu;
(e) a polypeptide selected from the group consisting of (Gly-Gly-Ser)$_q$, (Gly-Gly-Gly-Ser)$_r$, and (Gly-Gly-Gly-Gly-Ser)$_r$, (6-aminohexanoic acid)$_s$, (5-aminovaleric acid)$_s$, (7-aminoheptanoic acid)$_s$, and (8-aminooctanoic acid)$_s$, where q is any integer from 2 to 5, r is any integer from 1 to 3, and s is any integer from 4 to 15; and
(f) a conjugate linker wherein an amino polyethylene glycol carboxylate of Formula I as defined in (a) is conjugated with:

(i) an amino acid selected from the group consisting of Arg, Asn, Asp, Gln, Glu, His, Lys, Pro, Ser, Thr, Cit, Orn, Sar, Gly, γ-Abu and γ-Glu;
(ii) a dipeptide selected from the group consisting of Ala-Ala, β-Ala-β-Ala, Glu-Glu, Gly-Gly, Leu-Leu, Pro-Pro, Ser-Ser, Thr-Thr, γ-Glu-γ-Glu, Glu-γ-Glu, γ-Glu-Glu, γ-Abu-γ-Abu, 6-aminohexanoic acid-6-aminohexanoic acid, 5-aminovaleric acid-5-aminovaleric acid, 7-aminoheptanoic acid-7-aminoheptanoic acid and 8-aminooctanoic acid-8-aminooctanoic acid;
(iii) a tripeptide selected from the group consisting of Ala-Ala-Ala, β-Glu-Glu-Glu, γ-Glu-γ-Glu-γ-Glu, Glu-γ-Glu-γ-Glu, γ-Glu-γ-Glu-Glu, γ-Glu-Glu-γ-Glu, Gly-Gly-Gly, Gly-Gly-Ser, Ser-Gly-Gly, Gly-Ser-Gly, Gly-Gly-Glu, Glu-Gly-Gly, Gly-Glu-Gly, Gly-Gly-γ-Glu, γ-Glu-Gly-Gly, Gly-γ-Glu-Gly, Leu-Leu-Leu, Pro-Pro-Pro and γ-Abu-γ-Abu-γ-Abu; or
(iv) a polypeptide selected from the group consisting of (Gly-Gly-Ser)$_q$ (Gly-Gly-Gly-Ser)$_r$, and (Gly-Gly-Gly-Gly-Ser)$_r$, (6-aminohexanoic acid)$_s$, (5-aminovaleric acid)$_s$, (7-aminoheptanoic acid)$_s$, and (8-aminooctanoic acid)$_s$, where q is any integer from 2 to 5, r is any integer from 1 to 3, and s is any integer from 4 to 15.

3. The compound of claim 1, or a pharmaceutically acceptable salt thereof, wherein the linker is a conjugate linker, wherein an amino polyethylene glycol carboxylate of Formula I:

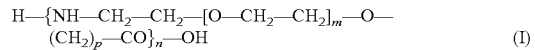

wherein m is any integer from 1 to 12, n is any integer from 1 to 12, and p is 1 or 2, is conjugated with:
(i) an amino acid selected from the group consisting of Arg, Asn, Asp, Gln, Glu, His, Lys, Pro, Ser, Thr, Cit, Orn, Sar, Gly, γ-Abu and γ-Glu;
(ii) a dipeptide selected from the group consisting of Ala-Ala, β-Ala-β-Ala, Glu-Glu, Gly-Gly, Leu-Leu, Pro-Pro, Ser-Ser, Thr-Thr, γ-Glu-γ-Glu, Glu-γ-Glu, γ-Glu-Glu, γ-Abu-γ-Abu, 6-aminohexanoic acid-6-aminohexanoic acid, 5-aminovaleric acid-5-aminovaleric acid, 7-aminoheptanoic acid-7-aminoheptanoic acid and 8-aminooctanoic acid-8-aminooctanoic acid;
(iii) a tripeptide selected from the group consisting of Ala-Ala-Ala, β-Ala-β-Ala-β-Ala, Glu-Glu-Glu, γ-Glu-γ-Glu-γ-Glu, Glu-γ-Glu-γ-Glu, γ-Glu-γ-Glu-Glu, γ-Glu-Glu-γ-Glu, Gly-Gly-Gly, Gly-Gly-Ser, Ser-Gly-Gly, Gly-Ser-Gly, Gly-Gly-Glu, Glu-Gly-Gly, Gly-Glu-Gly, Gly-Gly-γ-Glu, γ-Glu-Gly-Gly, Gly-γ-Glu-Gly, Leu-Leu-Leu, Pro-Pro-Pro and γ-Abu-γ-Abu-γ-Abu; or
(iv) a polypeptide selected from the group is selected from the group consisting of (Gly-Gly-Ser)$_q$ (Gly-Gly-Gly-Ser)$_r$, and (Gly-Gly-Gly-Gly-Ser)$_r$, (6-aminohexanoic acid)$_s$, (5-aminovaleric acid)$_s$, (7-aminoheptanoic acid)$_s$, and (8-aminooctanoic acid)$_s$, where q is any integer from 2 to 5, r is any integer from 1 to 3, and s is any integer from 4 to 15.

4. The compound of claim 3, or a pharmaceutically acceptable salt thereof, wherein n is 2, m is 1 and p is 1 for the amino polyethylene glycol carboxylate of Formula I.

5. The compound of claim 3, or a pharmaceutically acceptable salt thereof, wherein the amino polyethylene glycol carboxylate of Formula I is conjugated to an amino acid, wherein the amino acid is γ-Glu.

6. The compound of claim 3, or a pharmaceutically acceptable salt thereof, wherein the amino polyethylene glycol carboxylate of Formula I is conjugated to a dipeptide, wherein the dipeptide is γ-Glu-γ-Glu.

7. The compound of claim 3, or a pharmaceutically acceptable salt thereof, wherein the linker is ([2-(2-aminoethoxy)-ethoxy]-acetyl)$_2$-(γ-Glu)$_t$, wherein t is 1 or 2.

8. The compound of claim 1, or a pharmaceutically acceptable salt thereof, wherein the C14-C24 fatty acid is a saturated monoacid or saturated diacid selected from the group consisting of myristic acid (tetradecanoic acid)(C14 monoacid), tetradecanedioic acid (C14 diacid), palmitic acid (hexadecanoic acid)(C16 monoacid), hexadecanedioic acid (C16 diacid), margaric acid (heptadecanoic acid)(C17 monoacid), heptadecanedioic acid (C17 diacid), stearic acid (octadecanoic acid)(C18 monoacid), octadecanedioic acid (C18 diacid), nonadecylic acid (nonadecanoic acid)(C19 monoacid), nonadecanedioic acid (C19 diacid), arachadic acid (eicosanoic acid)(C20 monoacid), eicosanedioic acid (C20 diacid), heneicosylic acid (heneicosanoic acid)(C21 monoacid), heneicosanedioic acid (C21 diacid), behenic acid (docosanoic acid)(C22), docosanedioic acid (C22 diacid), lignoceric acid (tetracosanoic acid)(C24 monoacid) and tetracosanedioic acid (C24 diacid).

9. The compound of claim 8, or a pharmaceutically acceptable salt thereof, wherein the C14-C24 fatty acid is octadecanedioic acid.

10. The compound of claim 8, or a pharmaceutically acceptable salt thereof, wherein the C14-C24 fatty acid is eicosanedioic acid.

11. The compound of claim 8, or a pharmaceutically acceptable salt thereof, wherein the C-terminal amino acid is amidated.

12. A compound of the following formula:

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Glu-Gly-Gly-Pro-Ser-Ser-Gly wherein Xaa2 is Aib;
Lys at position 20 is chemically modified by conjugation of the epsilon-amino group of the Lys side chain with ([2-(2-aminoethoxy)-ethoxy]-acetyl)$_2$-(γ-Glu)-CO—(CH$_2$)$_{18}$CO$_2$H; and
the C-terminal amino acid is amidated (SEQ ID NO: 6); or a pharmaceutically acceptable salt thereof.

13. A pharmaceutical composition comprising the compound of claim 12, or a pharmaceutically acceptable salt thereof, and a pharmaceutically acceptable carrier, diluent, or excipient.

14. A method of treating type 2 diabetes in a subject in need thereof, comprising administering to the subject an effective amount of the compound of claim 12, or a pharmaceutically acceptable salt thereof.

15. A method of treating obesity in a subject in need thereof, comprising administering to the subject an effective amount of the compound of claim 12, or a pharmaceutically acceptable salt thereof.

16. A method of treating nonalcoholic fatty liver disease (NAFLD) in a subject in need thereof, comprising administering to the subject an effective amount of the compound of claim 12, or a pharmaceutically acceptable salt thereof.

17. A method of treating nonalcoholic steatohepatitis (NASH) in a subject in need thereof, comprising administering to the subject an effective amount of the compound of claim 12, or a pharmaceutically acceptable salt thereof.

18. A method of inducing non-therapeutic weight-loss in a subject comprising administration of an effective amount of the compound of claim 12, or a pharmaceutically acceptable salt thereof.

19. A compound of the following formula:

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Xaa28-Gly-Gly-Pro-Ser-Ser-Gly wherein
Xaa2 is Aib;
Xaa28 is Glu or Ser; and
the C-terminal amino acid is optionally amidated (SEQ ID NO: 9),
or a pharmaceutically acceptable salt thereof.

20. A process for the manufacture of a compound of the following formula:

His-Xaa2-Gln-Gly-Thr-Phe-Thr-Ser-Asp-Tyr-Ser-Lys-

Tyr-Leu-Asp-Glu-Lys-Lys-Ala-Lys-Glu-Phe-Val-Glu-

Trp-Leu-Leu-Xaa28-Gly-Gly-Pro-Ser-Ser-Gly wherein
Xaa2 is Aib;
Xaa28 is Glu or Ser;
Lys at position 20 is chemically modified by conjugation of the epsilon-amino group of the Lys side chain with a C14-C24 fatty acid via (i) a direct bond or (ii) a linker between the Lys at position 20 and the C14-C24 fatty acid; and
the C-terminal amino acid is optionally amidated (SEQ ID NO: 2), said process comprising the step of:
modifying the compound of claim 19 by conjugating the epsilon-amino group of the Lys side chain at position 20 of the compound of claim 19 with a C14-C24 fatty acid, optionally via a linker.

21. A compound produced by the process of claim 20, or a pharmaceutically acceptable salt thereof.

* * * * *

UNITED STATES PATENT AND TRADEMARK OFFICE
CERTIFICATE OF CORRECTION

PATENT NO. : 9,938,335 B2
APPLICATION NO. : 15/184116
DATED : April 10, 2018
INVENTOR(S) : Adam Robert Mezo et al.

Page 1 of 1

It is certified that error appears in the above-identified patent and that said Letters Patent is hereby corrected as shown below:

In the Claims

Column 52 Line 13. In Claim 2, delete "β-Glu-Glu-Glu," and insert -- β-Ala-β-Ala-β-Ala, Glu-Glu-Glu, --, therefor.

Signed and Sealed this
Nineteenth Day of June, 2018

Andrei Iancu
*Director of the United States Patent and Trademark Office*